(12) United States Patent
Noda et al.

(10) Patent No.: US 8,317,491 B2
(45) Date of Patent: Nov. 27, 2012

(54) HEATING/COOLING SYSTEM FOR INDWELLING HEAT EXCHANGE CATHETER

(75) Inventors: Wayne Noda, Mission Viejo, CA (US); Stelica Stelea, Yorba Linda, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 1287 days.

(21) Appl. No.: 11/765,564

(22) Filed: Jun. 20, 2007

(65) Prior Publication Data
US 2007/0240447 A1 Oct. 18, 2007

Related U.S. Application Data

(60) Division of application No. 10/913,127, filed on Aug. 6, 2004, now Pat. No. 7,287,398, which is a continuation-in-part of application No. 09/965,560, filed on Sep. 25, 2001, now Pat. No. 6,581,403.

(60) Provisional application No. 60/492,818, filed on Aug. 6, 2003.

(51) Int. Cl.
*F04B 17/00* (2006.01)

(52) U.S. Cl. ...................... 417/360; 417/413.1

(58) Field of Classification Search ............. 62/434; 604/131, 151; 417/319, 360, 363, 477.2; 248/222.52; 403/349
See application file for complete search history.

(56) References Cited

U.S. PATENT DOCUMENTS

| | | | | |
|---|---|---|---|---|
| 4,103,511 A * | 8/1978 | Kress et al. | ............. | 464/177 |
| 4,126,132 A * | 11/1978 | Portner et al. | ............. | 604/123 |
| 4,138,205 A * | 2/1979 | Wallach | ............. | 417/360 |
| 4,211,519 A * | 7/1980 | Hogan | ............. | 417/360 |
| 4,416,595 A * | 11/1983 | Cromie | ............. | 417/476 |
| 4,583,924 A * | 4/1986 | Zenglein et al. | ............. | 417/420 |
| 4,631,007 A * | 12/1986 | Olson | ............. | 417/476 |
| 4,631,008 A * | 12/1986 | Stenner | ............. | 417/477.1 |
| 4,653,987 A * | 3/1987 | Tsuji et al. | ............. | 417/360 |
| 4,735,558 A * | 4/1988 | Kienholz et al. | ............. | 417/477.2 |
| 4,758,228 A * | 7/1988 | Williams | ............. | 604/153 |
| 4,813,855 A * | 3/1989 | Leveen et al. | ............. | 417/477.9 |
| 4,913,703 A * | 4/1990 | Pasqualucci et al. | ............. | 604/153 |
| 5,044,902 A * | 9/1991 | Malbec | ............. | 417/477.2 |
| 5,062,775 A * | 11/1991 | Orth | ............. | 417/477.3 |
| 5,374,251 A * | 12/1994 | Smith | ............. | 604/151 |
| 5,404,614 A * | 4/1995 | Stephens | ............. | 15/327.2 |

(Continued)

OTHER PUBLICATIONS

Wayne Noda, "Heating/Cooling System for Indwelling Heat Exchange Catheter", File History of co-pending U.S. Appl. No. 11/765,536, filed Jun. 20, 2007.

(Continued)

*Primary Examiner* — Devon Kramer
*Assistant Examiner* — Alexander Comley
(74) *Attorney, Agent, or Firm* — John L. Rogitz

(57) ABSTRACT

A cooling system for an indwelling heat exchange catheter includes a heat exchange bath that is configured to receive a conduit that carries saline to and from the catheter. A heating/cooling fluid is in the bath and exchanges heat with the saline. The heating/cooling fluid flows through a heat exchanger that includes a refrigerant and two variable speed DC compressor for removing heat from the refrigerant. A gear pump circulates the working fluid to and from the catheter and is removably engaged with a pump support platform.

4 Claims, 17 Drawing Sheets

U.S. PATENT DOCUMENTS

| | | | | |
|---|---|---|---|---|
| 5,634,907 A | * | 6/1997 | Rani et al. | 604/151 |
| 5,840,068 A | * | 11/1998 | Cartledge | 604/131 |
| 5,857,843 A | * | 1/1999 | Leason et al. | 417/477.9 |
| 6,095,772 A | * | 8/2000 | Ramey et al. | 417/423.6 |
| 6,554,791 B1 | * | 4/2003 | Cartledge et al. | 604/67 |
| 2004/0208756 A1 | * | 10/2004 | Adahan | 417/360 |

OTHER PUBLICATIONS

Wayne Noda, "Heating/Cooling System for Indwelling Heat Exchange Catheter", File History of co-pending U.S. Appl. No. 11/765,579, filed Jun. 20, 2007.

* cited by examiner

HEATING/COOLING SYSTEM FOR INDWELLING HEAT EXCHANGE CATHETER

RELATED APPLICATIONS

This is a divisional of U.S. patent application ser. No. 10/913,127, filed Aug. 6, 2004, now U.S. Pat. No. 7,287,398 which is a continuation in part of U.S. patent application Ser. No. 09/965,560, filed Sep. 25, 2001, now U.S. Pat. No. 6,581,403, and which also claimed benefit of U.S. provisional application No. 60/492,818, filed Aug. 6, 2003.

BACKGROUND OF THE INVENTION

1. Field of the Invention

The present invention relates generally to methods and apparatus for exchanging heat with the body of a patient.

2. Description of the Related Art

It has been discovered that the medical outcome for a patient suffering from severe brain trauma or from ischemia caused by stroke or heart attack is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patents already are intubated with central venous catheters for other clinically approved purposes anyway such as drug delivery and blood monitoring, providing a central venous catheter that can also cool or heat the blood requires no additional surgical procedures for those patients. However, single purpose heat exchange catheters such as are made by Innercool Therapies of San Diego, Calif. and Radiant Medical of Portola Valley, Calif. can also be less optimally used.

Regardless of the particular catheter used, it is clear that heat must be removed from or added to the coolant that flows through the catheter. As recognized herein, it is desirable that a heat exchange system for a heat exchange catheter consume minimal energy and space. Small size is desired because space is often at a premium in critical care units. Moreover, as also recognized herein, for patient comfort it is desirable that such a heat exchange system generate a minimum amount of noise. As still further understood by the present invention, it is desirable that the heat exchange system be easy to use by health care personnel, and provide for monitoring systems and convenient temperature control. U.S. Pat. No. 6,146,411, incorporated herein by reference, discloses one such heat exchange system. It is the object of the present invention to still further address one or more of the above-noted considerations.

SUMMARY OF THE INVENTION

A heat exchange system for an indwelling heat exchange catheter includes a heat exchange bath that is configured to receive a conduit that carries working fluid to and from the catheter. A heating/coolant fluid is disposed within the bath to exchange heat with the working fluid. The heating/coolant fluid flows through a heat exchanger that includes a refrigerant and two or more compressors that are connected in parallel to each other. Moreover, a heating/coolant fluid pump circulates the heating/coolant fluid between the heat exchanger and the heat exchange bath.

In a preferred embodiment, the compressors are variable speed direct current (DC) compressors. Also, a positive displacement gear pump preferably pumps the working fluid, e.g., saline, to and from the catheter. In a preferred embodiment, the pump is removably engaged with a motor.

In another aspect of the present invention, a heat exchange system for an indwelling heat exchange catheter includes a heat exchange bath that is configured to receive a conduit that carries working fluid to and from the catheter, A pump communicates with the conduit and pumps the working fluid to and from the catheter.

In yet another aspect of the present invention, a fluid pump assembly includes a pump support platform. A pump is removably engaged with the pump support platform. In this aspect, the pump pumps working fluid to and from an intravascular catheter.

In still another aspect of the present invention, a heat exchange system for an indwelling heat exchange catheter includes a heat exchange bath that is configured to receive a conduit that carries working fluid to and from the catheter. In this aspect of the present invention, a flow detector communicates with the conduit and detects when working fluid is flowing through the conduit.

In yet still another aspect of the present invention, a fluid flow detector includes
a clear housing and a paddle wheel that is rotatably disposed within the housing. The fluid flow detector further includes three infrared transmitter/receiver light emitting diode pairs. Each infrared transmitter/receiver light emitting diode pair establishes a signal path through the housing.

The details of the present invention, both as to its construction and operation, can best be understood in reference to the accompanying drawings, in which like numerals refer to like parts, and which:

DETAILED DESCRIPTION OF THE PREFERRED EMBODIMENT

Description of the Heating/Cooling System

Figure 1:
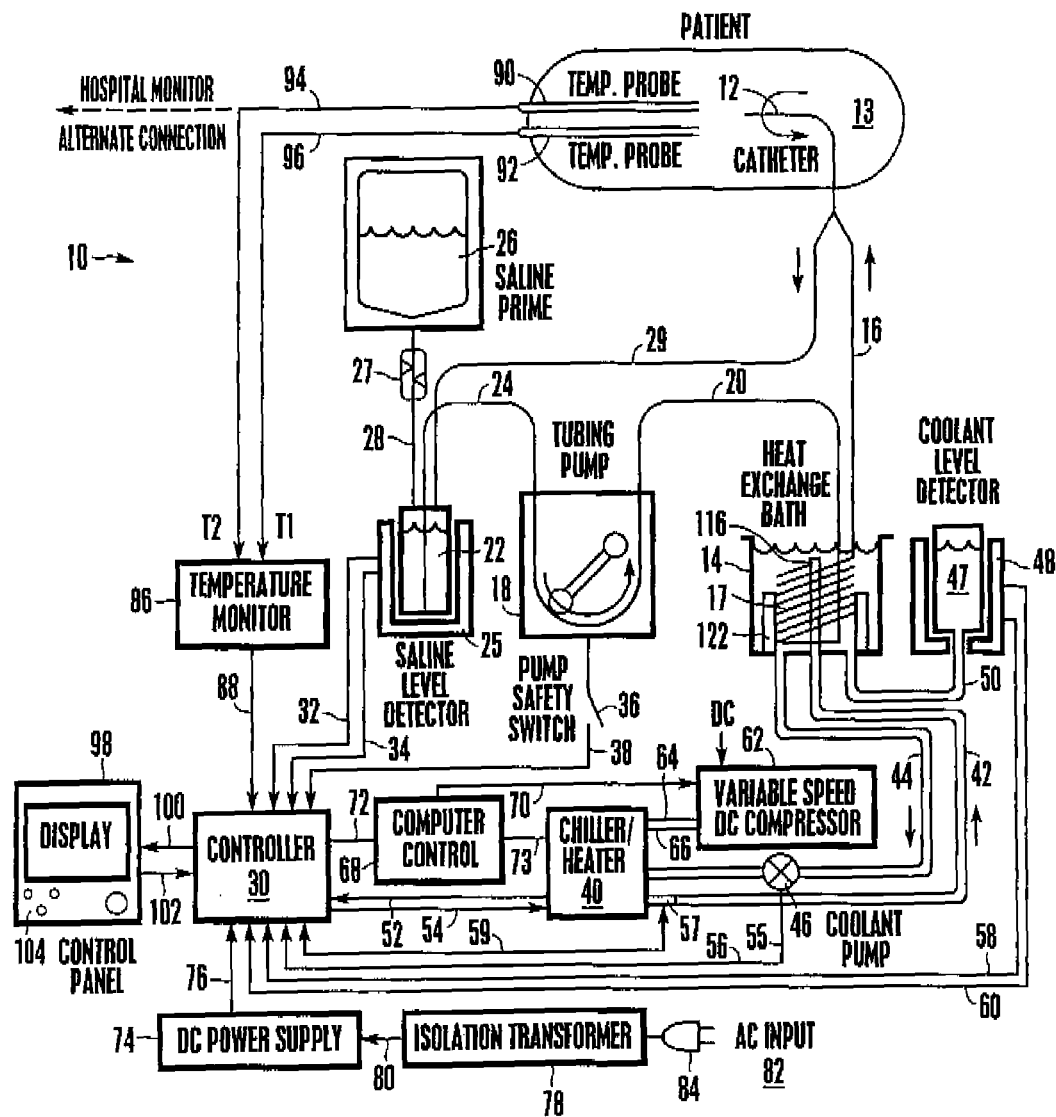
FIG. 1 is a schematic diagram of a heating/cooling system in accordance with the present invention.

Referring initially to FIG. 1, a patient heating/cooling system is shown and generally designated 10. As shown, the system 10 includes three separate fluid circuits: a saline circuit (also referred to as the working fluid circuit), a water glycol circuit (also referred to as the heating/cooling fluid circuit), and a refrigerant circuit (also referred to as the refrigerating fluid circuit.)

Taking the saline circuit first, an indwelling heat exchange catheter 12 that can be inserted into a patient 13 during an operation is connected to a heat exchange bath 14 by a saline supply line 16. The supply line 16 is connected to a coiled or helical heat exchange tube 17 that is immersed in the bath 14 fluid to exchange heat therewith. In turn, the heat exchange tube 17 is connected to a peristaltic tubing saline pump 18 by fluid line 20. Preferably, the saline pump 18 draws saline from a saline reservoir 22 via fluid line 24. As shown, the saline reservoir 22 is disposed within a saline level detector 25 that, as described in detail below, helps control the saline pump 18 based on the level of saline in the level reservoir 22. It is to be understood that in a preferred embodiment, the saline pump 18 has four modes: a standby or off mode, two treatment modes (i.e., two treatment speeds), and an idle mode wherein the saline pump 18 operates very slowly, but does not stop. In the idle mode, the patient 13 is effectively thermally decoupled from the heating/cooling system 10.

As further shown in FIG. 1, a saline source 26 provides saline to the saline reservoir 22 via fluid line 28. In a preferred embodiment, the saline source 26 is an intravenous (IV) bag and a line clamp 27 is installed on fluid line 28 between the saline source 26 and the saline reservoir 22. It is to be understood that after the saline reservoir 22 is filled the line clamp 27 is clamped on fluid line 28 to isolate the saline source 26 from the saline reservoir 22. FIG. 1 shows a saline return line 29 communicates saline from the catheter 12 to the saline reservoir 22 to complete the saline circuit. It is to be appreciated that the tubes 16, 17, 20, 24, and 29 can be provided as a disposable IV tubing set.

FIG. 1 also shows a system controller 30 that is connected to the saline level detector 25 via electrical line 32 and electrical line 34, i.e., one for each infrared detector that is associated with the saline level detector 25 as described below. Preferably, the system controller 30 is also connected to a safety switch 36 of the saline pump 18 via electrical line 38. As described in further detail below, the system controller 30 receives signals from the saline level detector 25 regarding the level of saline therein and uses this information to control the saline pump 18, including opening the safety switch 36 to de-energize the saline pump 18 under certain low saline level conditions.

It is to be understood that within the same circuit, saline is circulated to and from the catheter 12 through the helical heat exchange tube 17 in the heat exchange bath 14. As described in detail below, the heat exchange bath 14 is filled with heating/cooling fluid, preferably water glycol. The water glycol can be heated or cooled in order to heat or cool the saline and thus, increase or decrease the temperature of the patient 13 into which the catheter 12 is inserted. Also, it is to be understood that the preferred working fluid is saline, but any similar fluid well known in the art can be used.

Now considering the water glycol circuit, the water glycol circuit communicates with a chiller/heater 40 via a water glycol supply line 42 and a water glycol return line 44. A water glycol pump 46 is installed in the water glycol return line 44 to circulate water glycol through the water glycol circuit. FIG. 1 shows that the heat exchange bath 14 is also in fluid communication with a water glycol reservoir 47 installed within a water glycol level detector 48 via fluid line 50. In accordance with principles described below, the water glycol level detector 48 is used to determine the level of water glycol within the heat exchange bath 14.

Further, the system controller 30 is connected to the chiller/heater 40 via electrical lines 52 and 54. Moreover, the system controller 30 is connected to a safety switch 55 at the water glycol pump 46 via electrical line 56 and to the coolant level detector 48 via electrical line 58 and electrical line 60. Thus, the system controller 30 can control the operation of the chiller/heater 40 based on signals from a temperature monitor, described below, and control the operation of the water glycol pump 46 based on level signals from infrared detectors, also described below, that are disposed within the water glycol level detector 48. As shown, the system controller 300 is also connected to a temperature sensor 57 placed at the outlet of the chiller/heater via electrical line 59. The controller 30 uses input from the temperature sensor 57 to control the chiller/heater 40 and other system 10 components.

It is to be understood that as the water glycol is pumped through the water/glycol circuit the chiller/heater 40 can beat or cool the water glycol. Within the heat exchange bath 14, the water glycol exchanges heat with the saline. Thus, the water glycol can be used to heat or cool saline and in turn, heat or cool the patient in which the catheter 12 is intubated. It is to be further understood that water glycol is the preferred heating/cooling fluid. However, any other fluid with similar properties can be used.

Now considering the third (refrigerant) circuit, a variable speed direct current (DC) compressor 62 is in fluid communication with the chiller/heater 40 via a refrigerant supply line 64 and a refrigerant return line 66. It is to be understood that the compressor 62 is filled with refrigerant, e.g., R134a. A compressor controller 68 is connected to the compressor 62 via an electrical line 70. In turn, the system controller 30 is connected to the compressor controller 68 via electrical line 72. The compressor controller 68 is also connected to a heater, described below, within the chiller/heater 40 via electrical line 73.

It is to be understood that the system controller 30 receives temperature signals from the temperature monitor, described below, and uses these signals to control the operation of the compressor 62 and the heater. The compressor 62 is used to cool the water glycol that is pumped through the chiller/heater 40 by the water glycol pump 46.

Continuing to refer to FIG. 1, a DC power supply 74 is connected to the system controller 30 by an electrical line 76. In turn, the DC power supply 74 preferably is connected to an isolation transformer (XFMR) 78 by electrical line 80. The XFMR 78 can be connected to an alternating current (AC) input 82, e.g., a standard one hundred and twenty volt (120V) wall outlet, via a power cord 84. The system 10 can also be configured to work accommodate one hundred to two hundred and forty volts AC (100-240 VAC).

As further shown in FIG. 1, a temperature monitor 86 is connected to the system controller 30 via an electrical line 88, A first patient temperature probe 90 and a second patient temperature probe 92 preferably are connected to the temperature monitor 86 via electrical lines 94 and 96, respectively. As intended herein, the temperature monitor 86 uses the temperature probes 90, 92 to monitor the temperature of the patient 13. Moreover, the temperature monitor 86 sends signals to the system controller 30 representing the temperature of the patient 13. These signals are used by the system controller 30 to control the operation of the chiller/heater 40, the saline pump 18, and the DC compressor 62.

FIG. 1 shows a display device 98 that is connected to the system controller 30 via electrical line 100 and electrical line 102. Preferably, the display device 98 provides a visual indication of the patient's temperature and the bath temperature. For example, the display device 98 can be used to output graphs of minute by minute patient temperature (for, e.g., twenty one days) and water glycol bath temperature. the display device 98 can also be used to provide information regarding the cooling power required by the patient, whether the system is heating or cooling the bath, and at which rate, e.g., low, medium, or maximum, the system is heating or cooling the bath. Further, the display device 98 can display the current patient temperature and the patient target temperature.

It is to be understood that a user can scroll the graphs left or right with respect to a stationary cursor within the center of the display. As the graphs are scrolled, information corresponding thereto can be displayed. As shown, the display device 98 also includes a control panel 104 to allow a user, i.e., a doctor or a nurse, to input data, such as a target patient temperature, to the system 10.

Description of the Heat Exchange Bath

Figure 2:
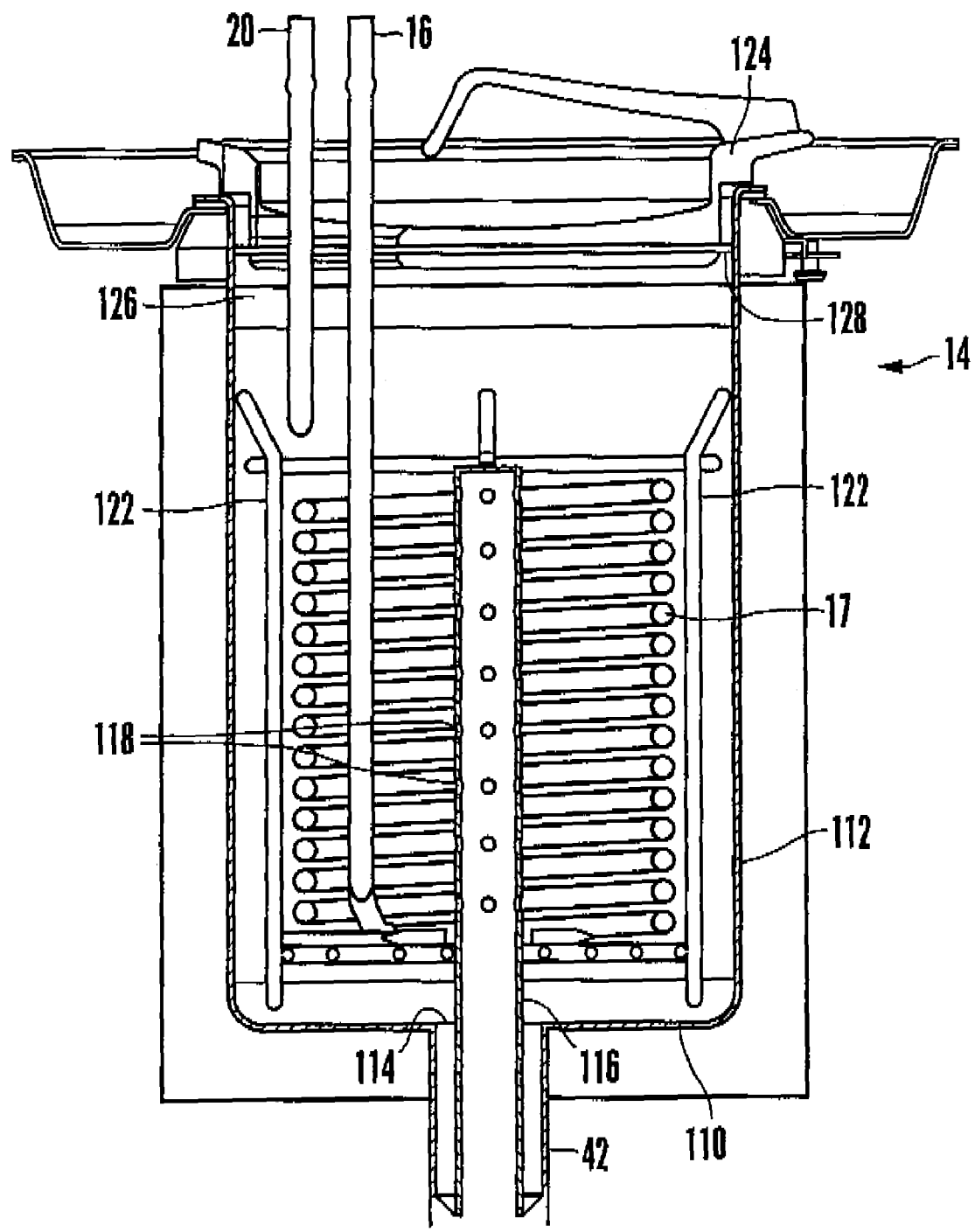
FIG. 2 is a cross-sectional view of a heat exchange bath with the water glycol return line and level detector omitted for clarity.

Referring now to FIG. 2, details of one preferred, non-limiting heat exchange bath 14 are shown. FIG. 2 shows that the preferred heat exchange bath 14 includes a bottom 110 having a generally cylindrical continuous sidewall 112 extending therefrom. As shown, the bottom 110 of the bath 14 is formed with a hole 114 and the water glycol supply line 42 is connected thereto. A preferably vertical standpipe 116 extends from the end of the water glycol supply line 42 into the interior of the bath 14. In a preferred embodiment, the standpipe 116 is perforated along its length with a series of four hole rings 118 out of which water glycol flows into the bath 14. These four hole rings 118 ensure radial movement of the water glycol through the heat exchange tubing 17, i.e., between and across the turns of the coil. It can be appreciated that in lieu of the standpipe 116, a small impeller (not shown) can be mounted on the bottom 110 of the bath 14 to circulate the water glycol therein.

As shown in FIG. 2, the generally spiral-shaped heat exchange tubing 17 is disposed within the bath 14 such that when the bath 14 is filled with water glycol the heat exchange tubing 17 is fully immersed in the water glycol. FIG. 2 shows that the saline supply line 16 is connected to one end of the heat exchange tubing 17. Conversely, the fluid line 20 from the saline pump 18 is connected to the other end of the heat exchange tubing 17. As shown, to center and support the spiral-shaped tubing set 120 around the standpipe 116, four vertical stanchions 122 (only two shown in FIG. 2) extend up from the bottom 110 of the bath 14 and touch the outer surface of the tubing set 120. In the alternative, the heat exchange tubing 17 can rest against the sidewall 112 of the bath 14.

FIG. 2 further shows that the bath 14 is covered by a lid 124. Preferably, the bottom of the lid 124 is spaced above the top of the water glycol within the bath 14 in order to establish a dead air space 126 between the lid 124 and the water glycol. This dead air space 126 acts as an insulator to minimize parasitic heat loads, control the evaporation of the water glycol, and prevent progressive overfilling of the bath 14 by condensation from the ambient air. Also, the lid 124 can be sealed against the wall 112 by a resilient, preferably silicone, gasket 128.

Description of the Level Detector

Figure 3:
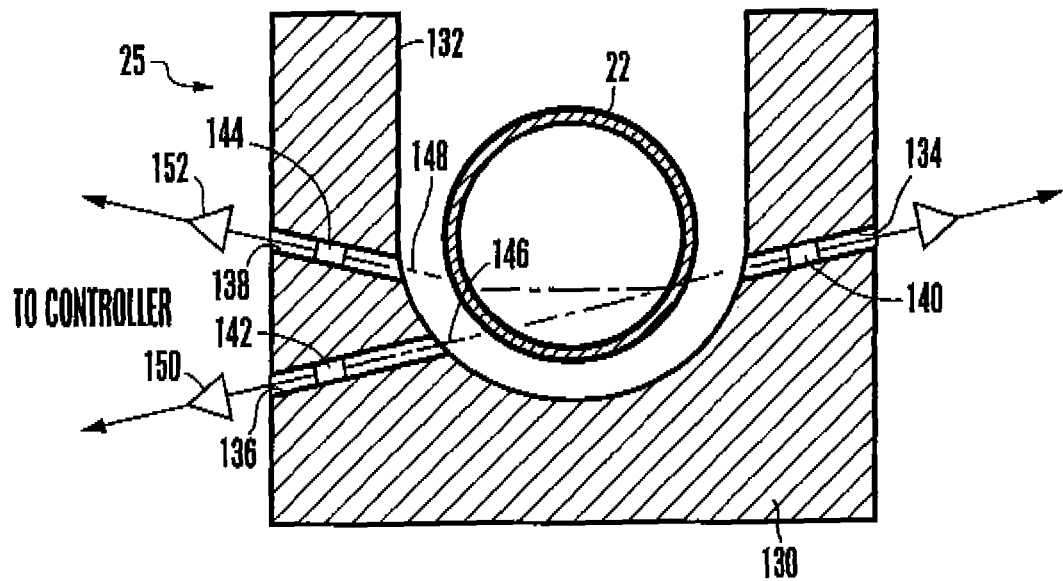
FIG. 3 is a cross-sectional view of a fluid level detector.

Referring now to FIG. 3, details of the preferred embodiment of the saline level detector 25 are shown. It is to be understood that the water glycol level detector 48 operates using the same principles as the saline level detector 25. As shown in FIG. 3, the saline level detector 25 includes a housing 130 that is preferably made from acetal, e.g., Deirin® manufactured by E.I. Dupont De Nemours & Co. of Delaware. The housing 130 is formed with a preferably "U" shaped central bore 132 in which the preferably clear saline reservoir 22 is disposed. FIG. 3 shows that the housing is formed with a first transverse bore 134, a second transverse bore 136, and a third transverse bore 138 leading to the central bore 132.

As shown, the saline level detector 25 includes a light emitter, e.g., an infrared light emitting diode (IR LED) 140, that is mounted in the first bore 134 on one side of the level detector 22. On the other hand, preferably two light detectors, such as a first IR detector 142 and a second IR detector 144, are placed on the opposite side of the saline level detector 25 from the LED 140 within the second and third transverse bores 136, 138. Preferably, the detectors 142, 144 are photodiodes or phototransistors.

In the presently preferred embodiment, IR LED 140 and the IR detectors 142, 144 are coplanar. Preferably, the IR LED 140 emits an IR light beam that can be detected by the first IR detector 142 if the saline level is below a predetermined level, e.g., the level of the IR LED 140 and the IR detectors 142, 144. In other words, if the saline is low, the IR light beam takes the path toward the first IR detector 142 as indicated by the dashed line 146. Conversely, if the saline is at the proper level within the saline level detector 25, the IR light beam is refracted so that it is detected by the second IR detector 144. In this case, the IR light beam takes the path indicated by line 148.

It is to be understood that the IR light beam can be modulated, i.e. pulsed, e.g., at nine and a half kiloHertz (9.5 kHz), to avoid false detections caused, e.g., by other light sources placed in the same room as the level detector 25 and/or bubbles in the saline reservoir 22. For this purpose, the first JR detector 142 and second IR detector 144 can be connected to upper and lower tone detectors 150, 152, respectively, which output signals only when they receive an input of; e.g., 9.5 kHz. It can be appreciated that when the saline level within the level detector falls below a predetermined level, the controller 30 can activate an alarm at the display device 98. The alarm can include a visible alarm, e.g., a light, or an audible alarm, e.g., a buzzer. Moreover, when the saline level drops below the predetermined level the controller 30 can de-energize the saline pump 18 by opening the safety switch 36.

Description of the Chiller/Heater

Figure 4:
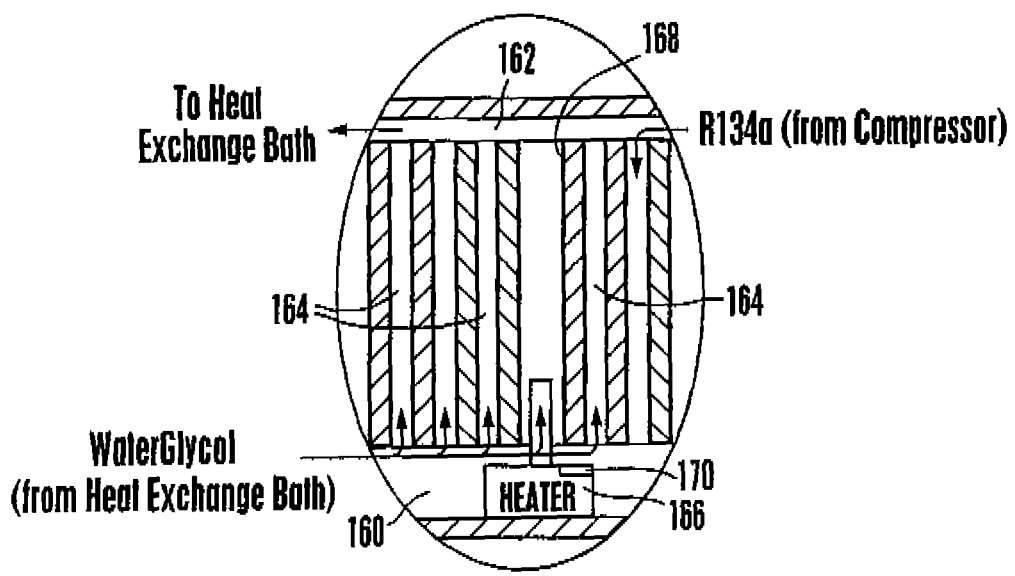
FIG. 4 is a detailed cross-sectional view of a chiller/heater.

FIG. 4 shows the details regarding one preferred, non-limiting implementation of the chiller/heater 40. As shown in FIG. 4, the chiller/heater 40 is a shell-and-tube heat exchanger having a lower chamber 160, an upper chamber 162, and plural tubes 164 communicating water glycol therebetween. It is to be understood that water glycol flows into the lower chamber 160, up the tubes 164, into to the upper chamber 162, and out of the upper chamber 162 to the heat exchange bath 14. Refrigerant, e.g., R134a, flows around the tubes 164 to cool the water glycol therein. A resistive heater element 166 is disposed in the lower chamber 160 and extends partially up an enlarged center tube 168 for heating the water glycol in the chiller/heater 60. As shown, the heater element 166 can include a built-in thermocouple temperature sensor 170 that can be used as described in detail below to determine if glycol is flowing through the chiller/heater 60. It is to be appreciated that in a less preferred embodiment the chiller/heater 40 and the heat exchange bath 14 can be combined into a single unit. Moreover, it is to be appreciated that the temperature sensor 170 can be connected to the system controller.

Description of the Overall Operation Logic of the Present Invention

Figure 5:
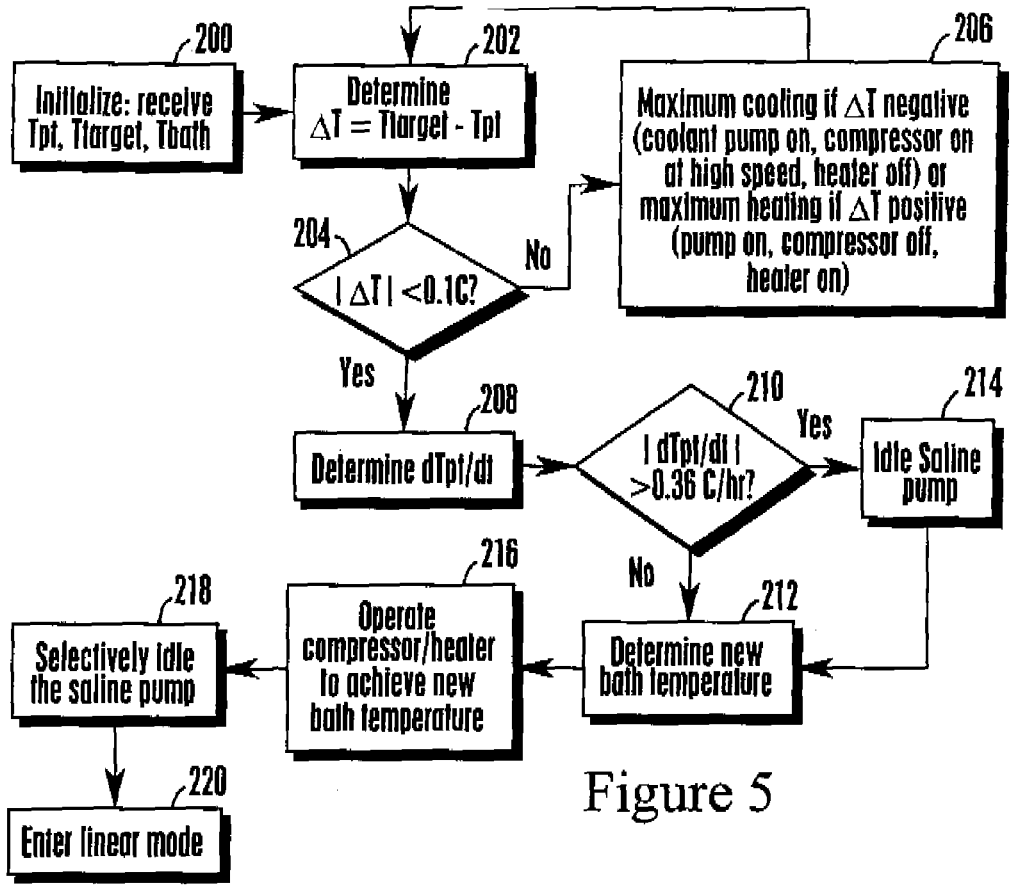
FIG. 5 is a flow chart of the overall operation logic of the present invention.

Referring now to FIG. 5, the overall operation logic of the present invention is shown and commences at block 200 wherein the controller 30 is initialized and the patient temperature ($T_{pt}$), the patient target temperature ($T_{target}$), and the bath temperature ($T_{bath}$) are received. Preferably, $T_{pt}$ is received from the temperature monitor 86, specifically from the second temperature probe 92. Moving to block 202, a temperature differential, $\Delta T$, is determined by subtracting $T_{pt}$ from $T_{target}$. Next, at decision diamond 204 it is determined whether the absolute value of $\Delta T$ is less than a predetermined amount, e.g., one tenth of a degree Celsius (0.1° C.).

If the absolute value of $\Delta T$ is greater than 0.1° C., the logic moves to block 206 where the system 10 enters maximum cooling mode or maximum warning mode. It is to be understood that if $\Delta T$ is negative the saline pump 18 is brought to full speed, the compressor 62 is turned on at high speed, and the heater 166 is turned off to cool the patient. Conversely, if $\Delta T$ is positive, the saline pump 18 is brought to full speed, the compressor 62 is turned off, and the heater 166 is turned on to warm the patient.

Returning to decision diamond 204, if the absolute value of $\Delta T$ is less than 0.1° C., the logic moves to block 208 where the rate of change of $T_{pt}$ with respect to time, $dT_{pt}/dt$, is determined using the following equation:

$$\left[\sum_{i=1}^{n}\left(\frac{n+1}{2}\right)-i*T_{pt}(i)\right]/\left[n*\left(\frac{1-n^2}{12}\right)\right]$$

where,
n=10 unless there has not yet been 10 minutes worth of patient temperature data
$T_{pt}$=Patient temperature From block 208, the logic moves to decision diamond 210 where it is determined whether the absolute value of $dT_{pt}/dt$ is greater than thirty six hundredths of a degree Celsius per hour (0.36° C./hr). If not, the logic continues to block 212 and a new $T_{bath}$ is determined. The new $T_{bath}$ is determined based on the rate of change of patient temperature. A higher rate of change results in a new $T_{bath}$ that is further away from the current $T_{bath}$ and a lower rate of change results in a new $T_{bath}$ that is closer to the current $T_{bath}$. If $dT_{pt}/dt$ is indeed greater than 0.36° C./hr and negative, meaning that the patient 13 is being rapidly cooled and does not require saline circulation through the catheter, the logic moves to block 214 where the saline pump 18 is idled. Thereafter, the logic moves to 212 and a new $T_{bath}$ is determined.

After block 212, the logic proceeds to block 216, wherein the compressor 62 and chiller/heater 40 are operated in accordance with the rules set forth below to achieve the new $T_{bath}$. Continuing to block 218, in a preferred embodiment, the saline pump 18 is selectively idled per the following rules:

1. Condition: A warming treatment has just started and the water glycol temperature is lower than $T_{pt}$.
    Rule: The saline pump 18 idled until the water glycol temperature is at least as warm as $T_{pt}$.

2. Condition: A controlled heating/cooling rate treatment has just started and the water glycol temperature is not within one degree Celsius (1° C.) of the water glycol reference temperature, $T_{ref}$, ($T_{pt}$–6° C. when cooling, $T_{pt}$+1° C. when heating).
    Rule: The saline pump 18 is idled until the water glycol temperature is within 1° C. of $T_{ref}$.
3. Condition: $T_{pt}$ is within 0.1° C. of $T_{target}$ and $dT_{pt}/dt<0.36$° C./hr.
    Rule: The saline pump 18 is idled at a very low rate until the water glycol temperature reaches $T_{ref}$.
4. Condition: PID has been controlling the system, the error exceeds the overshoot threshold, and the water glycol temperature is warmer than $T_{pt}$.
    Rule: The saline pump 18 is idled until the water glycol temperature is lower than $T_{pt}$.
5. Condition: PID has been controlling the system, the error exceeds the undershoot threshold, and the water glycol temperature is cooler than $T_{pt}$.
    Rule: The saline pump 18 is idled until the water glycol temperature is higher than $T_{pt}$.

After the saline pump 18 is selectively idled as described above, the logic proceeds to block 220 where the system enters the linear cooling mode, described below.

Description of the Linear Mode Operation Logic of the Present Invention

Figure 6:
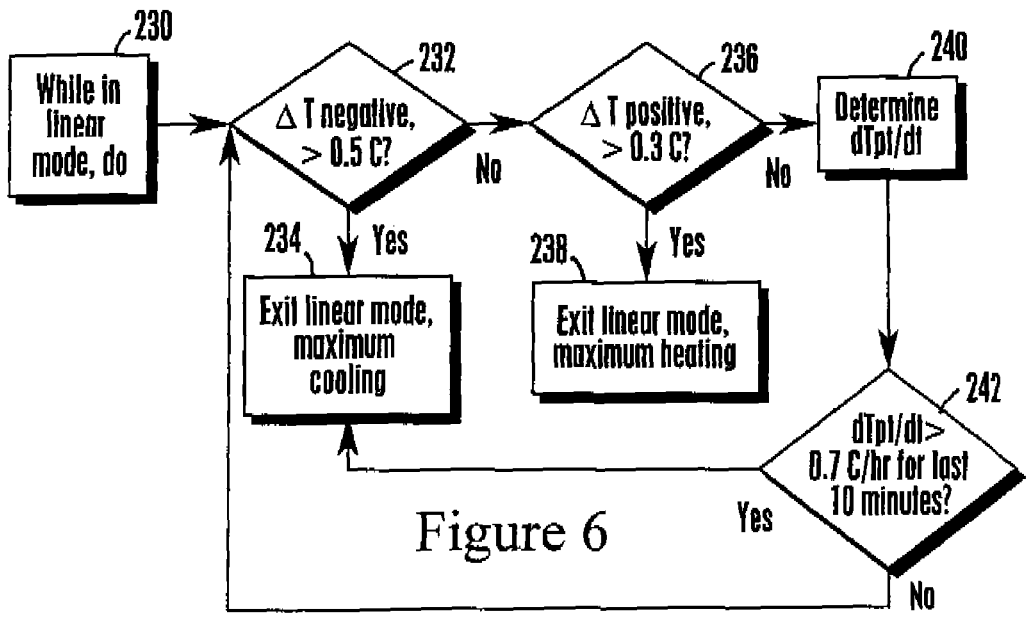
FIG. 6 is a flow chart of the linear mode operation logic of the present invention.

FIG. 6 shows the linear mode operation logic of the present invention. Commencing at block 230 a do loop is entered wherein while in the linear mode, the succeeding steps are performed. In the linear mode, several "fail safe" tests are monitored for to revert to maximum cooling or heating in the event that a rapid patient temperature change occurs. For instance, at decision diamond 232, if it is determined that $\Delta T$ is greater than one half a degree Celsius (0.5° C.) and has a negative sign, the system exits linear mode and enters maximum cooling mode at block 234. Also, if at decision diamond 236 it is determined that $\Delta T$ is positive and greater than three tenths of a degree Celsius (0.3° C.), the logic moves to block 238 where the linear mode is exited and the maximum warming mode is entered. Moreover, at block 240, $dT_{pt}/dt$ is determined using the equation described above.

Proceeding to decision diamond 242, it is determined whether $dT_{pt}/dt$ is greater than seven tenths of a degree Celsius per hour (0.7° C./hr) for the last ten (10) minutes. If so, the logic moves to block 234 where the linear mode is exited and the maximum cooling mode is entered. If $dT_{pt}/dt$ is less than 0.7° C./hr for the last 10 minutes, the logic returns to decision diamond 232 and continues as described above.

Description of the Compressor Control Logic of the Present Invention

Figure 7:
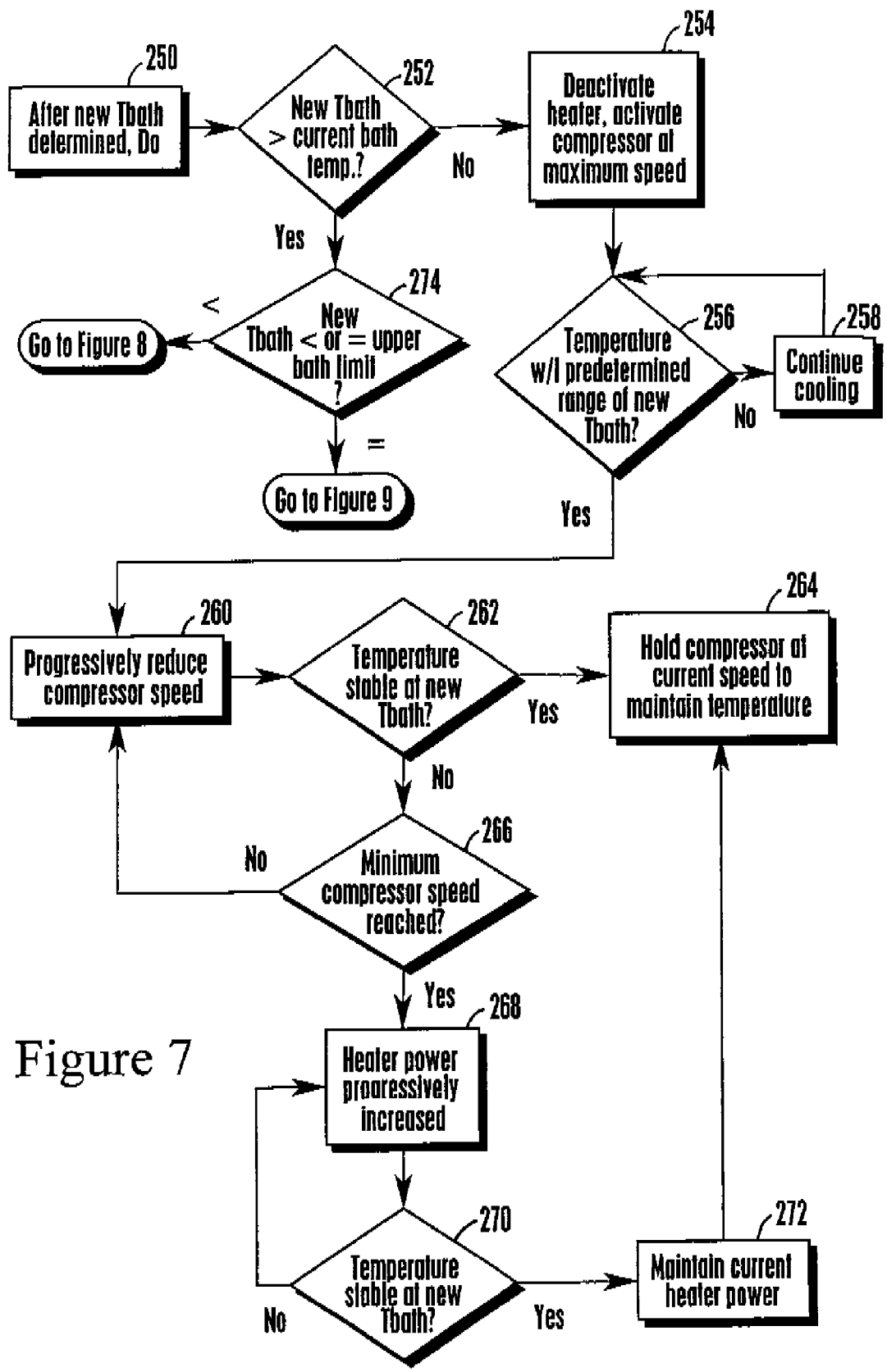
FIG. 7 is a flow chart of a first portion of the compressor control logic.

Referring now to FIG. 7, the control logic of the compressor is shown and commences at block 250 with a do loop, wherein after a new $T_{bath}$ is determined, the following steps are performed. At decision diamond 252, it is determined whether the new $T_{bath}$ is greater than the current $T_{bath}$. If the new $T_{bath}$ is lower than the current $T_{bath}$, the logic moves to block 254 and the heater 166 is deactivated while the compressor 62 is activated at maximum speed to cool the water glycol.

Continuing to decision diamond 256, it is determined whether the current bath temperature is within a predetermined range, e.g., two-tenths degrees Celsius (0.2° C.) of the new $T_{bath}$. If not, the logic moves to block 258 where the cooling of the water glycol is continued. The logic then returns to decision diamond 256. If the current bath temperature is within the predetermined range of the new $T_{bath}$, the logic moves to block 260 wherein the compressor speed is progressively reduced.

From block 260, the logic moves to decision diamond 262 where it is determined whether the current temperature is stable at the new $T_{bath}$. If so, the logic moves to block 264 and the compressor 62 is held at the current speed to maintain the temperature at the new $T_{bath}$. If, at decision diamond 262, the temperature has not stabilized at the new $T_{bath}$, the logic moves to decision diamond 266 where it is determined whether the minimum compressor speed has been reached. If the minimum compressor speed has not been reached, the logic returns to block 260 and continues as described above. Conversely, if the minimum compressor speed has been reached, the logic moves to block 268 where the heater power is progressively increased.

Next, the logic continues to decision diamond 270 where it is determined if the current temperature has stabilized at the new $T_{bath}$. If not, the logic returns to block 268 where the heater power continues to be progressively increased. If, on the other hand, the current temperature has stabilized at $T_{bath}$ the logic moves to block 272 where the current power is maintained. Thereafter, the logic moves to block 264 where the compressor is idled at the current speed, in this case the lowest speed, in order to maintain the temperature at $T_{bath}$. In a preferred, non-limiting embodiment, the lowest temperature to which the bath can be commanded is one-half degree Celsius (0.5° C.).

Returning to decision diamond 252, if the new $T_{bath}$ is greater than the current temperature, the logic proceeds to decision diamond 274 where it is determined whether the new $T_{bath}$ is less than or equal to a predetermined upper bath limit, e.g., forty two degrees Celsius (42° C.). If the new $T_{bath}$ is less than the upper bath limit, the logic moves to FIG. 8. However, if the new $T_{bath}$ is equal to the upper bath limit, the logic moves to FIG. 9.

Figure 8:
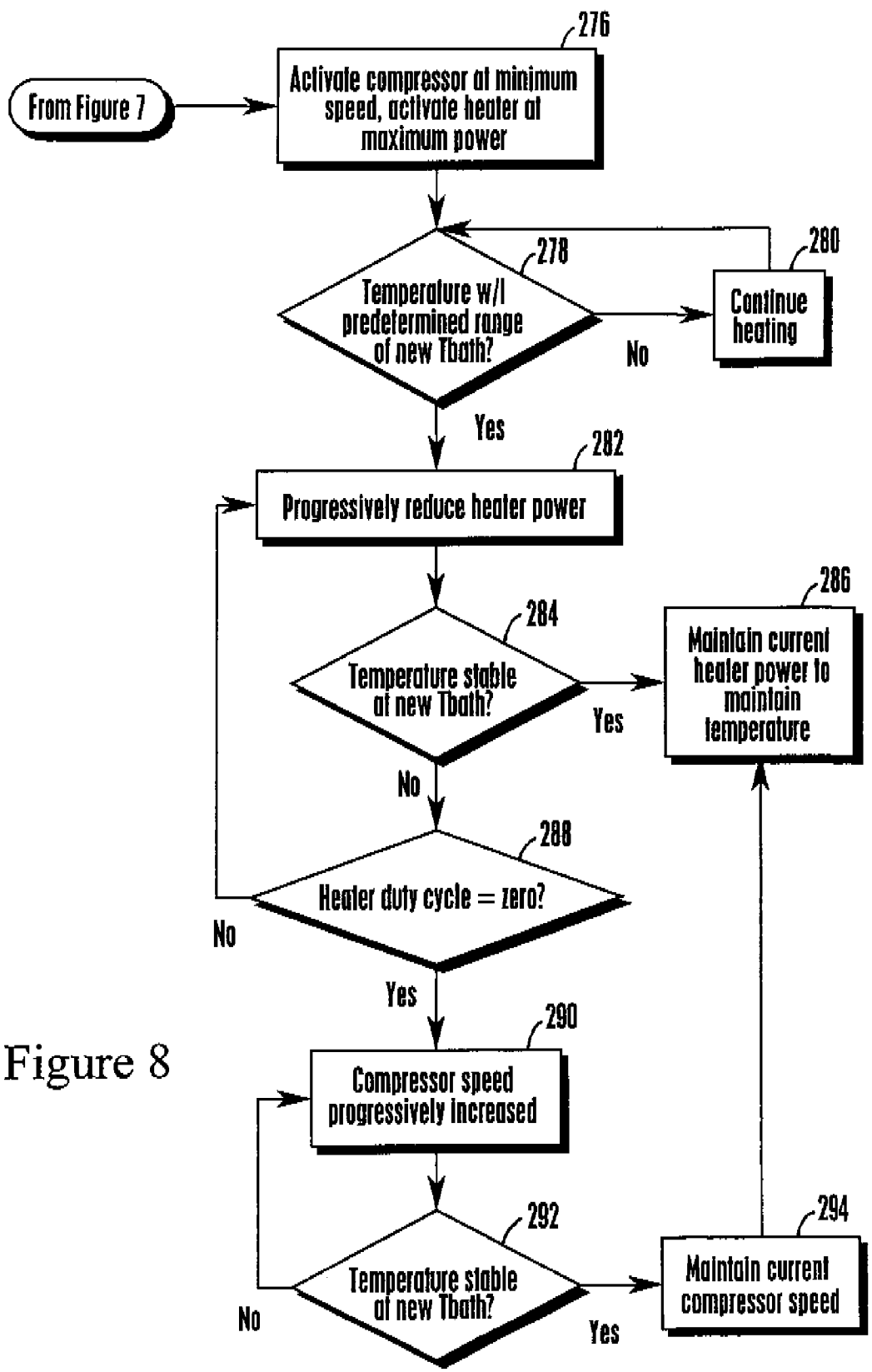
FIG. 8 is a flow chart of a second portion of the compressor control logic.

Proceeding to FIG. 8, if the new $T_{bath}$ is less than the upper bath limit, the logic proceeds to block 276 where the compressor 62 is activated at minimum speed and the heater 166 is activated at maximum power. From block 276, the logic moves to decision diamond 278 where it is determined if the current temperature is within a predetermined range, e.g., two-tenths degrees Celsius (0.2° C.) of the new $T_{bath}$. If not, the logic proceeds to block 280 and the heating of the water glycol is continued. If the temperature is within the predetermined range, the logic continues to block 282 where the heater power is progressively reduced.

Next, at decision diamond 284, it is determined whether the current temperature has stabilized at the new $T_{bath}$. If the current temperature has stabilized at the new $T_{bath}$, the current heater power is maintained to maintain the temperature at the new $T_{bath}$. On the other hand, if the current temperature has not stabilized, the logic proceeds to decision diamond 288 where it is determined if the heater duty cycle is equal to zero (0). If not, the logic returns to block 282 where the progressive reduction of the heater power is continued.

If, at decision diamond 288, the heater duty cycle is equal to zero, indicating that the lowest heating power has been reached, logic continues to block 290 where the speed of the compressor 62 is progressively increased. Thereafter, at decision diamond 292, it is determined whether the current temperature has stabilized at the new $T_{bath}$. If the temperature has not stabilized, the logic moves to block 290 where the reduction of the compressor speed is continued. On the other hand, if the temperature of the compressor speed has stabilized at $T_{bath}$ the logic continues to block 294 where the current compressor speed is maintained. The logic then moves to block 286 and ends.

Figure 9:
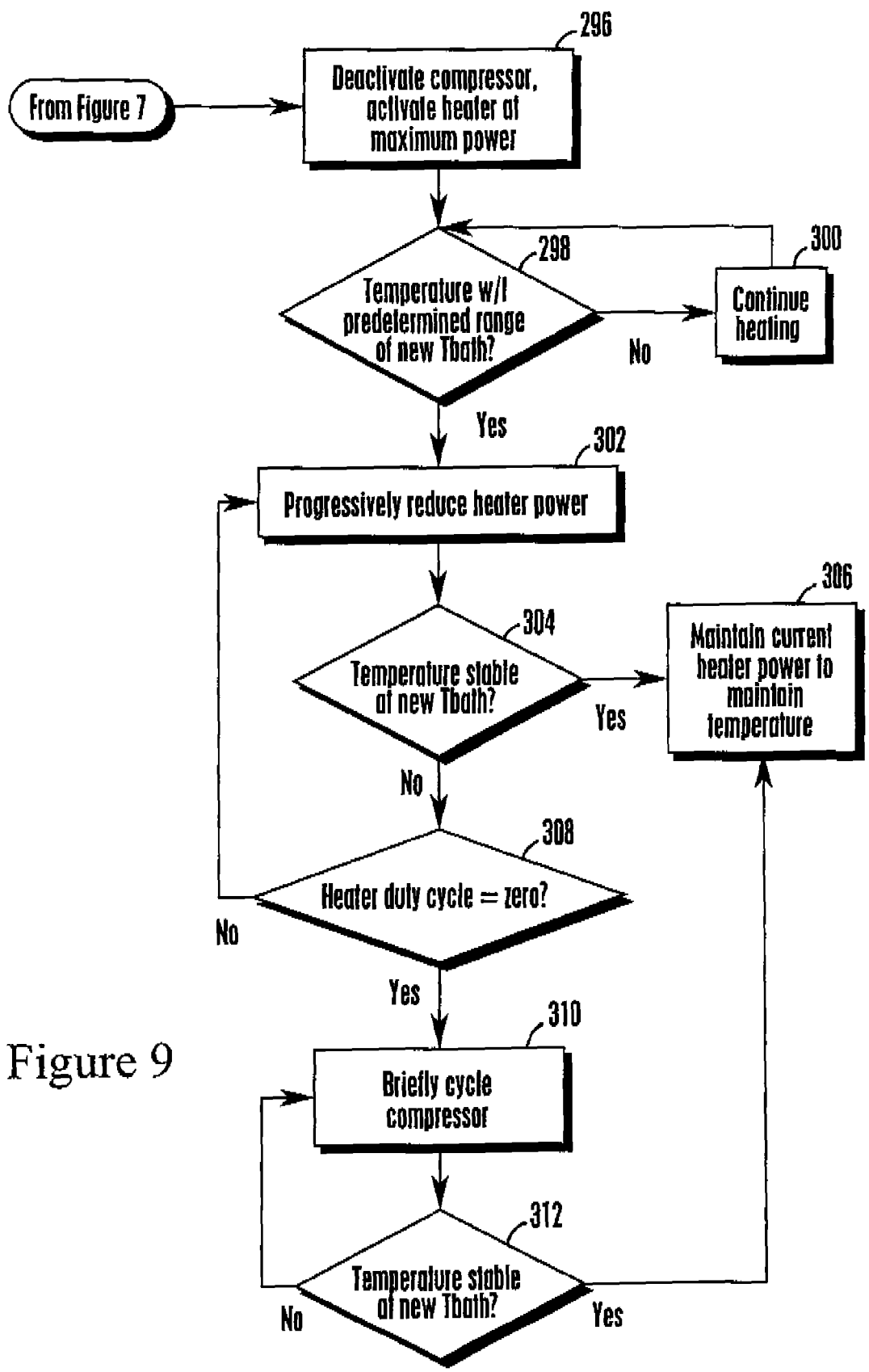
FIG. 9 is a flow chart of a third portion of the compressor control logic.

Returning to decision diamond 274 (FIG. 7), if the new $T_{bath}$ is equal to the upper bath limit, the logic moves to FIG. 9. At block 296, the compressor is deactivated and the heater is activated at maximum power. From block 296, the logic moves to decision diamond 298 where it is determined whether the temperature is within a predetermined range, e.g., two-tenths degrees Celsius (0.2° C.), of the new $T_{bath}$. If not, the heating of the water glycol is continued at block 300. If the current temperature is within 3° C. of the new $T_{bath}$ the logic proceeds to block 302 where the power of the heater 166 is progressively reduced. Then, at decision diamond 304, it is determined whether the temperature has stabilized at the new $T_{bath}$. If so, the current heater power is maintained to maintain the temperature at the new $T_{bath}$. Conversely, if the temperature has not stabilized at the new $T_{bath}$, the logic continues to decision diamond 308 where it is determined whether the heater duty cycle has reached zero (0). If the heater duty cycle has not reached zero, the logic returns to block 302 where the progressive reduction of the heater power is continued. On the other hand, if the heater duty cycle has reached zero, the compressor 62 is briefly cycled in order to cool the water glycol. Next, at decision diamond 312, it is again determined whether the temperature has stabilized at the new $T_{bath}$. If not, the logic returns to block 310 and the compressor is again briefly cycled to cool the water glycol. If, at decision diamond 312, the temperature has stabilized at the new $T_{bath}$, the logic moves to block 306 and ends.

It is to be understood that the system described above has two nested closed-loop controllers: an outer loop and an inner loop. The outer loop is directly responsible for controlling the patient temperature and is driven by the temperature difference between $T_{target}$ and $T_{pt}$. On the other hand, the inner loop is directly responsible for the coolant temperature, i.e., $T_{bath}$, that is established by the system controller 30. It is further to be understood that the outer loop logic, i.e., the overall operation logic and linear mode operation logic describe above, resides in the system controller 30. The inner loop control logic, i.e., the compressor control logic described above, resides in the compressor controller 68. As intended by the present invention, when the compressor controller 68 receives a command to establish a new $T_{bath}$, the compressor controller 68 controls the compressor 62 and the heater 166, as described above, in order to achieve the new $T_{bath}$.

In a preferred, non-limiting embodiment, the compressor controller 68 has two means of control over the compressor 62. First, it can turn the power to compressor 62 on and off via a solid-state DC relay. Second, it can modulate the compressor speed between a maximum value, e.g., thirty five hundred revolutions per minute (3,500 RPM), and a minimum value, e.g., two thousand revolutions per minute (2,000 RPM).

Also, in a non-limiting embodiment, the compressor controller 68 has only duty-cycle control over the heater 166. The compressor controller 68 can modulate the heater power anywhere between zero percent (0%), i.e., off, and one hundred percent (100%), i.e., on. Preferably, the heater 166 has a fixed one second (1 s) pulse period. Also, in a preferred embodiment the heater 166 has a maximum power of two hundred and forty watts (240 w). Thus, a fifty percent (50%) duty cycle corresponds to one hundred and twenty watts (120 w) of time-averaged input power to the water glycol and a twenty five percent (25%) duty cycle would correspond to sixty watts (60 w) of time-averaged input power.

Figure 10:
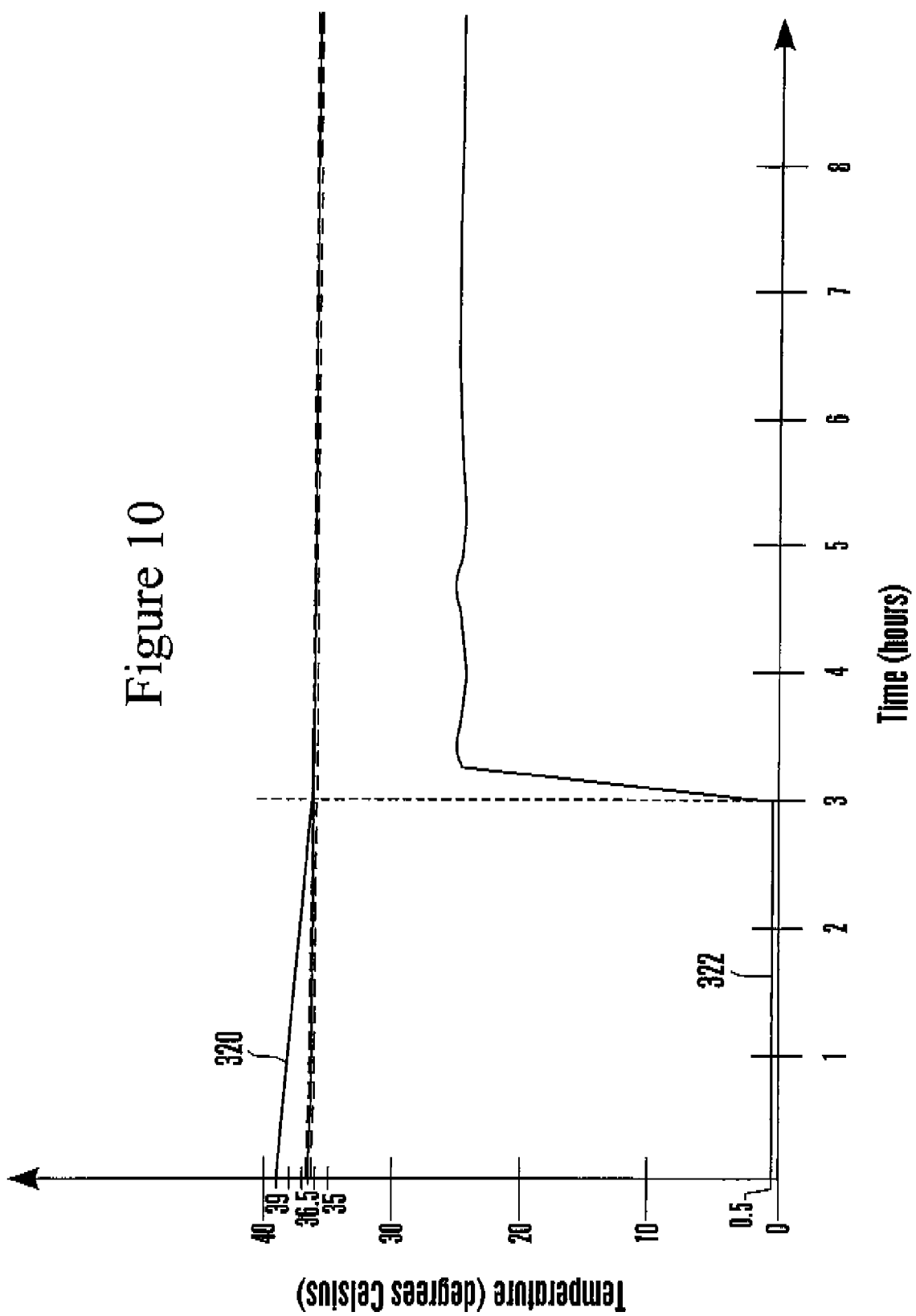
FIG. 10 is an exemplary graph of patient temperature and bath temperature versus time.

Description of an Exemplary Graph of Patient Temperature and Bath Temperature Versus Time FIG. 10 shows one exemplary, non-limiting graph of $T_{pt}$, represented by line 320, and $T_{bath}$, represented by line 322, plotted versus time. As shown, the patient is initially in a hyperthermic state, i.e., the patient has a fever of thirty-nine degrees Celsius (39° C.). The patient is cooled from 39° C. toward a $T_{target}$ equal to thirty-six and one-half degrees Celsius (36.5° C.) preferably over a three hour period at a rate of eight tenths of a degree Celsius per hour (0.80° C./hr). This can be achieved by entering a maximum cooling mode where the $T_{bath}$ is one-half a degree Celsius (0.5° C.).

Once $T_{pt}$ reaches thirty six and six tenth degrees (36.6° C.), the saline pump 18 preferably is idled to thermally de-couple the patient 13 from the cooling system 10 and the $T_{bath}$ is increased, e.g., by energizing the heater 166, to approximately twenty-five degrees Celsius (25° C.). By thermally de-coupling the patient 13 from the cooling system 10, $T_{pt}$ will discontinue the rapid decrease described above while $T_{bath}$ is increased.

After $T_{bath}$ reaches 25° C., the saline pump 18 is returned to full speed to thermally couple the patient 13 to the cooling system 20. As intended by the present invention, the higher $T_{bath}$ slows the rate at which the patient 13 is cooled and helps to maintain $T_{pt}$ in a state of equilibrium near $T_{target}$, e.g., within one-tenth of a degree Celsius (0.1° C.) of $T_{target}$. If necessary, $T_{bath}$ can be slightly increased or decreased, e.g., less than five degrees Celsius (5° C.), as shown in order to maintain $T_{pt}$ in the state of equilibrium described above.

Description of an Alternative Heating/Cooling System

Figure 11:
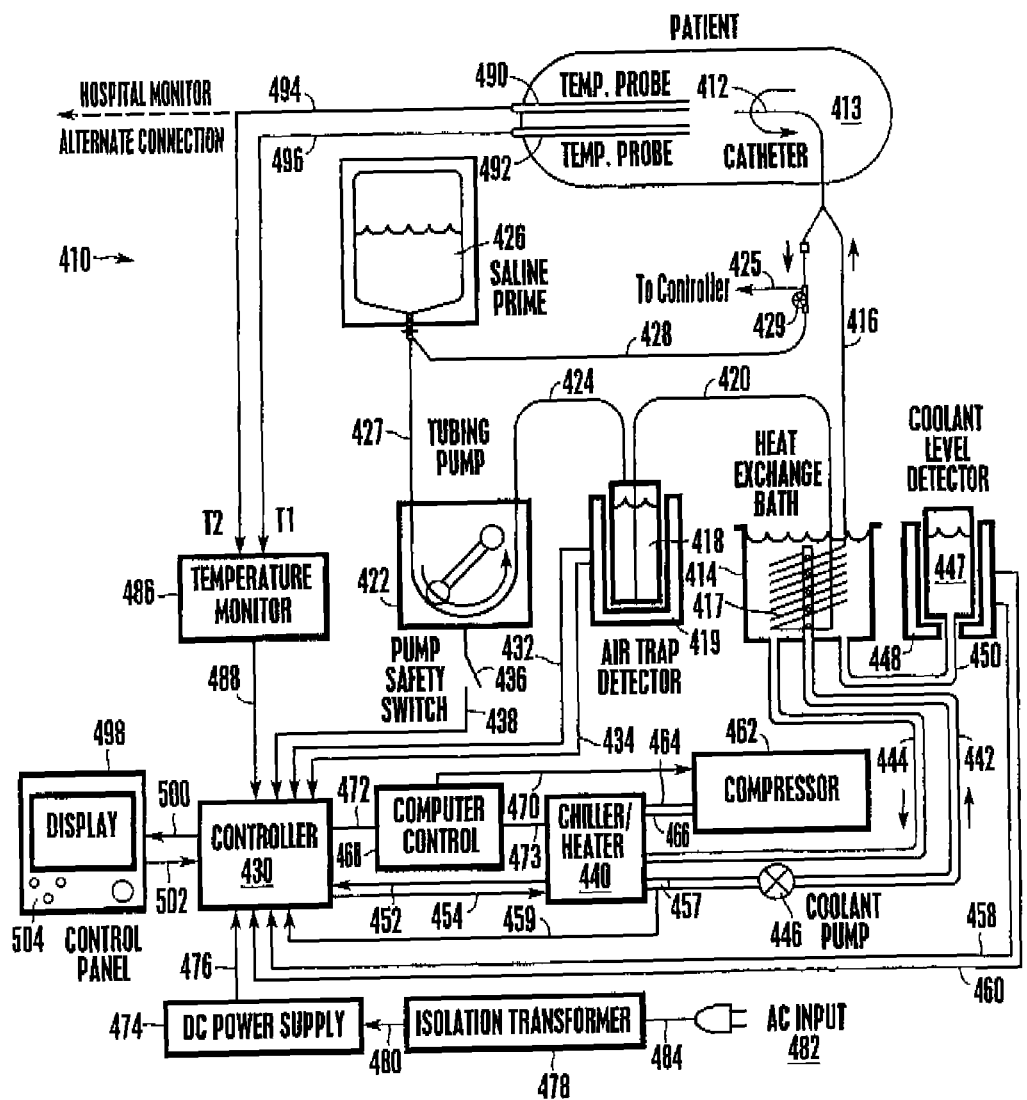
FIG. 11 is a schematic diagram of an alternative heating/cooling system.

Referring now to FIG. 11, an alternative patient heating/cooling system is shown and generally designated 410. Similar to the above-described system 10, the system 410 shown in FIG. 11 includes three separate fluid circuits: a saline circuit (also referred to as the working fluid circuit), a water glycol circuit (also referred to as the heating/cooling fluid circuit), and a refrigerant circuit (also referred to as the refrigerating fluid circuit.)

Taking the saline circuit first, an indwelling heat exchange catheter 412 that can be inserted into a patient 413 during an operation is connected to a heat exchange bath 414 by a saline supply line 416. The supply line 416 is connected to a coiled or helical heat exchange tube 417 that is immersed in the bath fluid to exchange heat therewith. In turn, the heat exchange tube 417 is connected an air trap vessel 418 by fluid line 420. The air trap vessel 418 is surrounded by an air trap detector 419. As shown, the air trap vessel 418 is connected to a saline pump 422 by fluid line 424.

It is to be understood that the air trap detector 419 is identical in construction to the saline level detector 25 described above and shown in FIG. 3 and can be used to detect when air is introduced into the working fluid circuit downstream from the pump 422, e.g., by the pump 422 itself. Accordingly, if air is detected in the air trap vessel 418, the pump 422 is immediately shut down by a controller in accordance with the principles discussed earlier.

As further shown in FIG. 11, a saline source 426 provides saline to the pump 422 via fluid line 427. FIG. 11 shows a saline return line 428 that communicates saline from the catheter 412 to the saline reservoir 426 to complete the saline circuit. A saline flow detector 429, described in detail below, is installed along the saline return line 428 between the catheter 412 and the saline reservoir 426. FIG. 11, shows that the saline flow detector 429 provides feedback to the system controller, described below, via electrical line 425.

FIG. 11 also shows a system controller 430 that is connected to the air trap detector 419 via electrical line 432 and electrical line 434, i.e., one for each infrared detector that is associated with the air trap detector 419. Preferably, the system controller 430 is also connected to a safety switch 436 of the saline pump 422 via electrical line 438. As described in further detail below, the system controller 430 receives signals from the air trap detector 419 regarding the level of saline therein and uses this information to control the saline pump 422, including opening the safety switch 436 to de-energize the saline pump 422 under certain low saline level conditions. It is to be understood that within the saline circuit, saline is circulated to and from the catheter 412 through the helical heat exchange tube 417 in the heat exchange bath 414.

Now considering the water glycol circuit, the water glycol circuit communicates with a chiller/heater 440 via a water glycol supply line 442 and a water glycol return line 444. A water glycol pump 446 is installed in the water glycol supply line 442 to circulate water glycol through the water glycol circuit. FIG. 11 shows that the heat exchange bath 414 is also in fluid communication with a water glycol reservoir 447 via fluid line 450. As shown, the water glycol reservoir is installed within a water glycol level detector 448. In accordance with the principles described above, the water glycol level detector 448 can be used to determine the level of water glycol within the heat exchange bath 414.

Further, the system controller 430 is connected to the chiller/heater 440 via electrical lines 452 and 454. Moreover, the system controller 430 is connected to the coolant level detector 448 via electrical line 458 and electrical line 460. Thus, the system controller 430 can control the operation of the chiller/heater 440 based on signals from a temperature monitor, described below, and control the operation of the water glycol pump 446 based on level signals from the infrared detectors that are disposed within the water glycol level detector 448. As shown, the system controller 430 is also connected to a temperature sensor 457 placed at the outlet of the chiller/heater via electrical line 459. The controller 430 uses input from the temperature sensor 457 to control the chiller/heater 440 and other system 410 components.

It is to be understood that as the water glycol is pumped through the water/glycol circuit the chiller/heater 440 can heat or cool the water glycol. Within the heat exchange bath 414, the water glycol exchanges heat with the saline. Thus, the water glycol can be used to heat or cool saline and in turn, heat or cool the patient in which the catheter 412 is installed. It is to be further understood that water glycol is the preferred heating/cooling fluid. However, any other fluid with similar properties can be used.

Now considering the third (refrigerant) circuit, a variable speed direct current (DC) compressor 462 is in fluid communication with the chiller/heater 440 via a refrigerant supply line 464 and a refrigerant return line 466. It is to be understood that the compressor 462 is filled with refrigerant, e.g., R134a. A compressor controller 468 is connected to the compressor 462 via an electrical line 470. In turn, the system controller 430 is connected to the compressor controller 468 via electrical line 472. The compressor controller 468 is also connected to a heater (FIG. 4) within the chiller/heater 440 via electrical line 473.

It is to be understood that the system controller 430 receives temperature signals from the temperature monitor, described below, and uses these signals to control the operation of the compressor 462 and the heater. The compressor 462 is used to cool the water glycol that is pumped through the chiller/heater 440 by the water glycol pump 446.

Continuing to refer to FIG. 11, a DC power supply 474 is connected to the system controller 430 by an electrical line 476. In turn, the DC power supply 474 preferably is connected to an isolation transformer (XFMR) 478 by electrical line 480. The XFMR 478 can be connected to an alternating current (AC) input 482, e.g., a standard one hundred and twenty volt (120V) wall outlet, via a power cord 484. It can be appreciated that a power supply having a low current leakage can be used and if it is indeed used, the XFMR 478 can be eliminated.

As further shown in FIG. 11, a temperature monitor 486 is connected to the system controller 430 via an electrical line 488. A first patient temperature probe 490 and a second patient temperature probe 492 preferably are connected to the temperature monitor 486 via electrical lines 494 and 496, respectively. As intended herein, the temperature monitor 486 uses the temperature probes 490, 492 to monitor the temperature of the patient 413. Moreover, the temperature monitor 486 sends signals to the system controller 430 representing the temperature of the patient 413. These signals are used by the system controller 430 to control the operation of the chiller/heater 440, the saline pump 418, and the DC compressor 462.

FIG. 11 shows a display device 498 that is connected to the system controller 430 via electrical line 500 and electrical line 502. Preferably, the display device 498 can provide a visual indication of the patient's temperature and the bath temperature. For example, the display device 498 can be used to output graphs of minute by minute patient temperature (for, e.g., twenty one days) and water glycol bath temperature. The display device 498 can also be used to provide information regarding the cooling power required by the patient, whether the system is heating or cooling the bath, and at which rate, e.g., low, medium, or maximum, the system is beating or cooling the bath. Further, the display device 498 can display the current patient temperature and the patient target temperature.

It is to be understood that a user can scroll the graphs left or right with respect to a stationary cursor within the center of the display. As the graphs are scrolled, information corresponding thereto can be displayed. As shown, the display device 498 also includes a control panel 504 to allow a user, i.e., a doctor or a nurse, to input data, such as a target patient temperature, to the system 410.

Description of an Alternative Refrigerating Fluid Circuit

Figure 12:
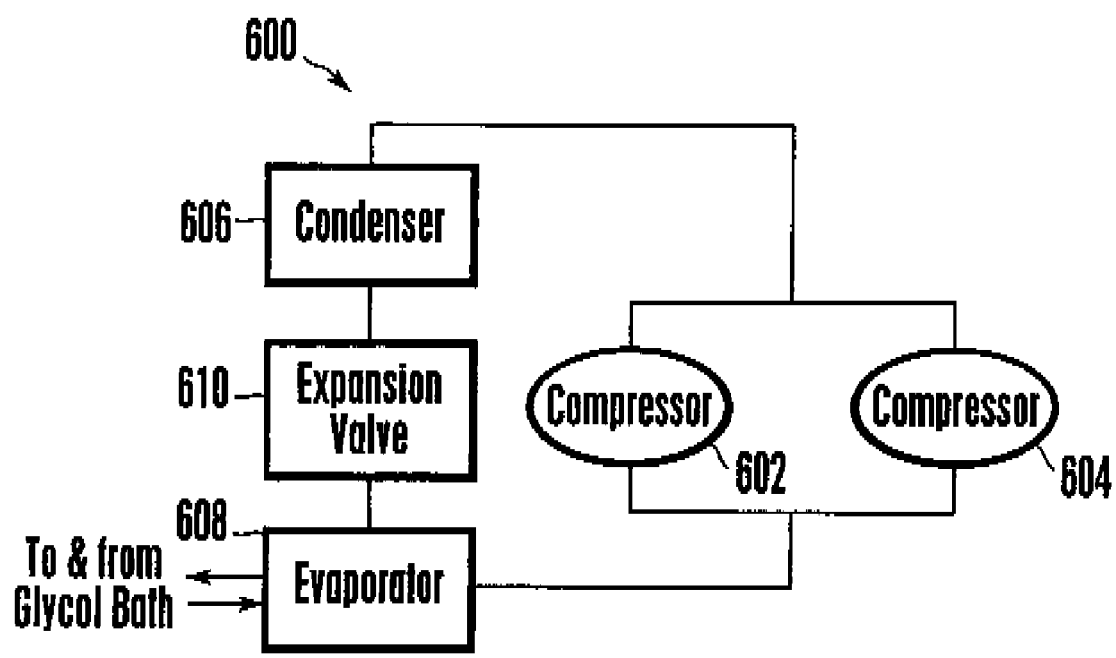
FIG. 12 is a schematic diagram of an alternative refrigerating fluid circuit.

Referring to FIG. 12 an alternative refrigerating fluid circuit is shown and is generally designated 600. FIG. 12 shows that the refrigerating fluid circuit 600 includes a first compressor 602 and a second compressor 604 that are connected in parallel to each other and connected in series to a condenser 606 and an evaporator 608. An expansion valve 610 is also connected between the condenser 606 and the evaporator 608 to complete the fluid circuit. As shown in FIG. 12, glycol is pumped to and from the evaporator 608 from a glycol bath. In a preferred embodiment, the compressors 602, 604 are variable speed direct current (dc) compressors that can be controlled by a controller, e.g., a computer or any other microprocessor. In order to prevent one or both of the compressors 602, 604 from stalling during operation, the controller preferably includes an algorithm that can prevent either compressor from being energized when the other compressor is fully loaded. It can be appreciated that the two compressors 602, 604 working in parallel with each other increase the cooling power of the refrigerating fluid circuit 600.

Description of a Saline Pump Assembly

Figure 13:
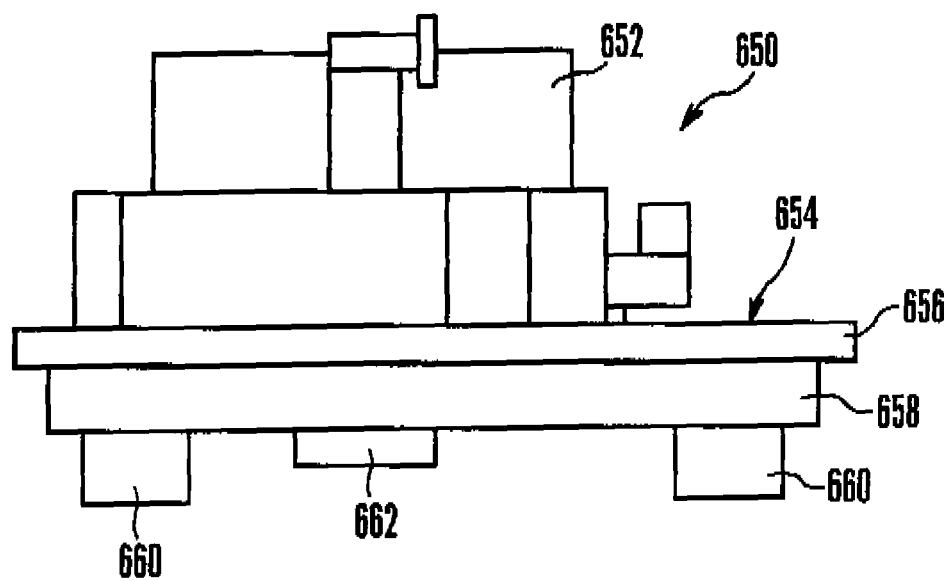
FIG. 13 is a side plan view of a saline pump assembly.
Figure 14:
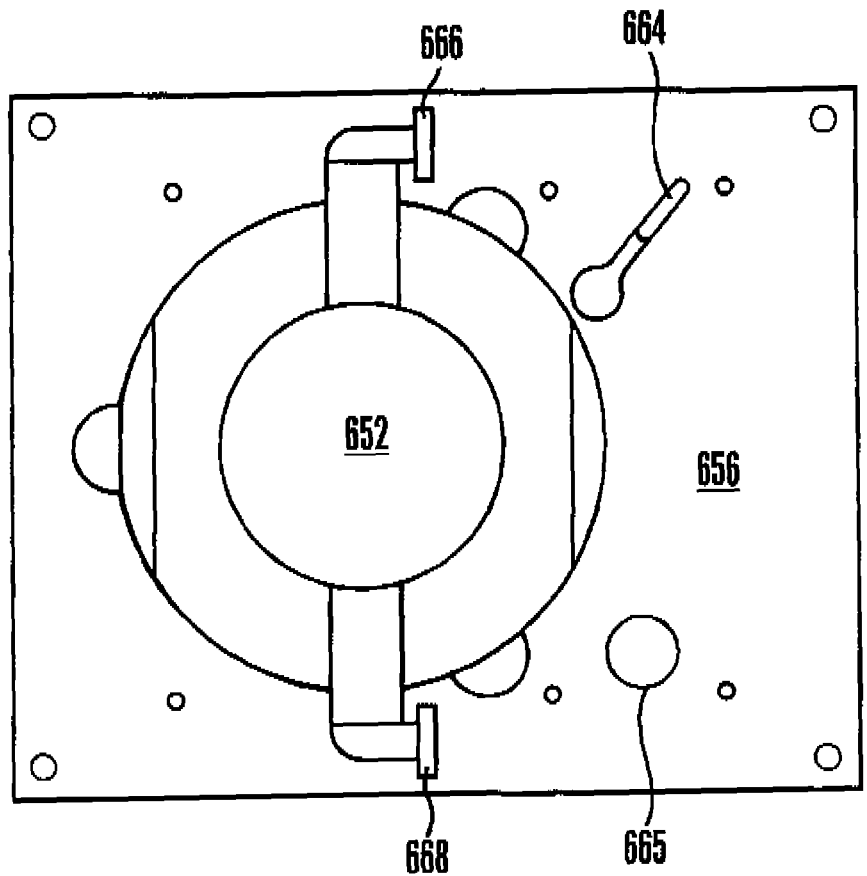
FIG. 14 is a top plan view of the saline pump assembly.

FIGS. 13 and 14 show an exemplary, non-limiting saline pump assembly, generally designated 650. As shown in FIGS. 13 and 14, the pump assembly 650 includes a diaphragm pump 652 that is removably engaged with a pump support platform 654. In one non-limiting embodiment, the pump 652 is similar to the high efficiency diaphragm pump disclosed in U.S. Pat. Nos. 5,791,882 and 5,800,136, incorporated herein by reference.

FIG. 13 shows that the pump support platform 654 includes an upper plate 656 and a lower plate 658 that, in a preferred embodiment, are attached to each other, e.g., by threaded fasteners. As shown in FIG. 13, plural feet 660 extend from the lower plate 658 and provide stable support for the pump support platform 654. FIG. 13 also shows that a pump drive assembly 662 is incorporated into the lower plate 658 of the pump support platform 654. The pump drive assembly 662 includes a motor and a drive shaft, described below, that extends through the upper plate 656 of the pump support platform 654 and engages the pump 650.

Figure 15:
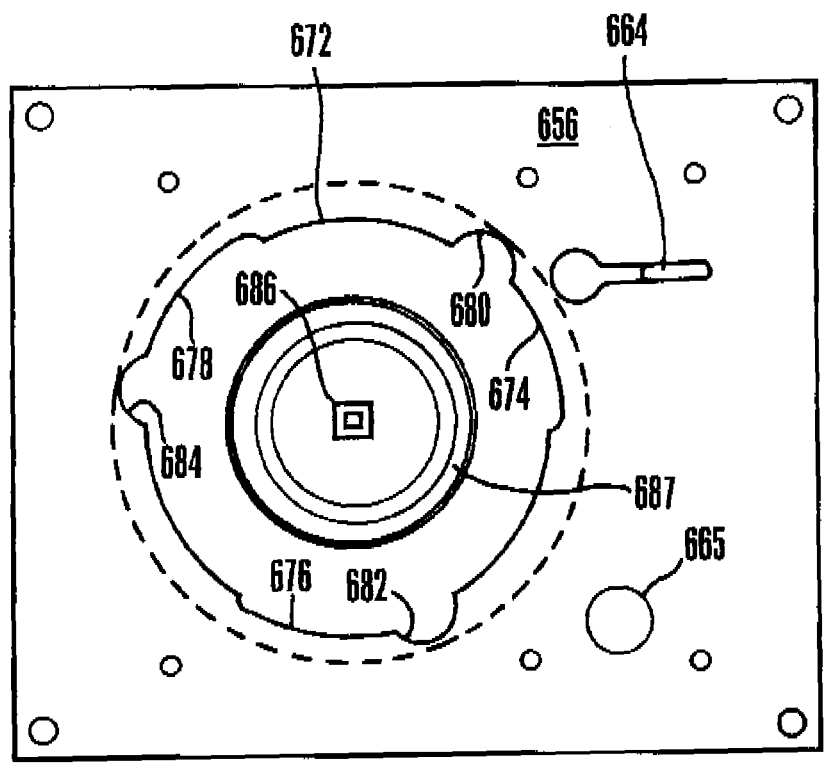
FIG. 15 is a top plan view of a pump support platform.

As shown in FIGS. 13 and 14, the pump support platform 654 includes a quick-release locking arm 664 that prevents the pump 652 from being disengaged with the pump support platform 654—unless the locking arm 664 is rotated to release the pump 652. FIGS. 14 and 15 also show that the pump support platform 654 includes an overflow bore 665 through which any saline that may leak from the pump 652 can flow. FIG. 14 further shows that the pump 652 includes an inlet 666 and an outlet 668. As discussed above, the pump 652, i.e., the outlet 668 thereof, can be connected to the air trap vessel 418 (FIG. 11) that is downstream from the pump 652.

Referring now to FIG. 15, further details concerning the pump support platform 654 are shown. FIG. 15 shows that the upper plate 656 of the pump support platform 654 is formed with a generally cylindrical pump locking bore 672. The outer periphery of the pump locking bore 672 is radially formed with a first slot 674, a second slot 676, and a third slot 678. As shown, each slot 674, 676, 678 is equally spaced around the outer periphery of the pump locking bore 672. Also, each slot 674, 676, 678 is curved to match the radius of curvature of the pump locking bore 672 and each slot 674, 676, 678 terminates in a semi-cylindrical bay 680, 682, 684. FIG. 15 also shows that a drive shaft 686 extends from the pump drive assembly 662 (FIG. 13) through the upper plate 656. It is to be understood that the pump drive assembly 662 includes a motor 687 for rotating the drive shaft 686. The motor 687 can be directly connected to the drive shaft 686, as shown, or it can be geared thereto.

Figure 16:
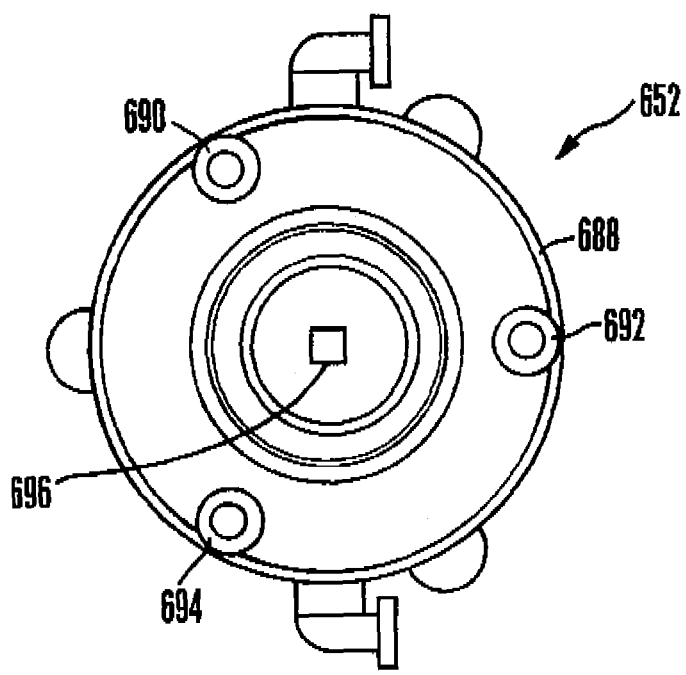
FIG. 16 is a bottom plan view of a pump.

FIG. 16 shows further details concerning the construction of the pump 652. As shown, the pump 652 includes a generally cylindrical lower housing 688. A first generally cylindrical leg 690, a second generally cylindrical leg 692, and a third generally cylindrical leg 694 are equally spaced around the periphery of the lower housing 688. FIG. 16 shows that the pump 652 further includes a drive shaft receptacle 696 into which the drive shaft 686 (FIG. 15) extends when the pump 652 is removably engaged with the pump support platform 654. It is to be understood that the drive shaft 686 is keyed to the drive shaft receptacle 696.

It can be appreciated that the pump 652 can be engaged with the pump support platform 654 by aligning the cylindrical legs 690, 692, 694 with the semi-cylindrical bays 680, 682, 684 established by the pump locking bore 672. The drive shaft 686 is also aligned with the drive shaft receptacle 696. In this relationship, the pump 652 can be slid toward the pump support platform 654 until the lower housing 688 of the pump 652 contacts the upper plate 656 of the pump support platform 654. The pump 652 is then rotated within the pump locking bore 672 until each leg 690, 692, 694 of the pump 652 reaches a respective end of each slot 674, 676, 678 formed by the pump locking bore 672. It is to be understood that during installation of the pump 652 on the pump support platform 654, one leg 690, 692, 694 of the pump 652 (any leg, thereof) rides against and then past the quick-release locking arm 664 until the quick-release locking arm 664 clears the leg 690, 692, 694 and snaps under spring bias to a position to prevent the pump 652 from being removed from the pump support platform 654.

In accordance with the principles of the present invention, a pump 652 can be easily engaged and disengaged with the pump support platform 654 during use. Thus, a first sterilized pump can be used in conjunction with the treatment of a first patient. After treatment has concluded, the now-used pump can be removed and replaced with a second sterilized pump to be used in conjunction with the treatment of a second patient. The pump support platform 654 (and the motor therein) need not be replaced for each new pump and the costs of utilizing the heat/cooling system of the present invention are reduced.

Description of an Alternative Saline Pump Assembly

Figure 17:
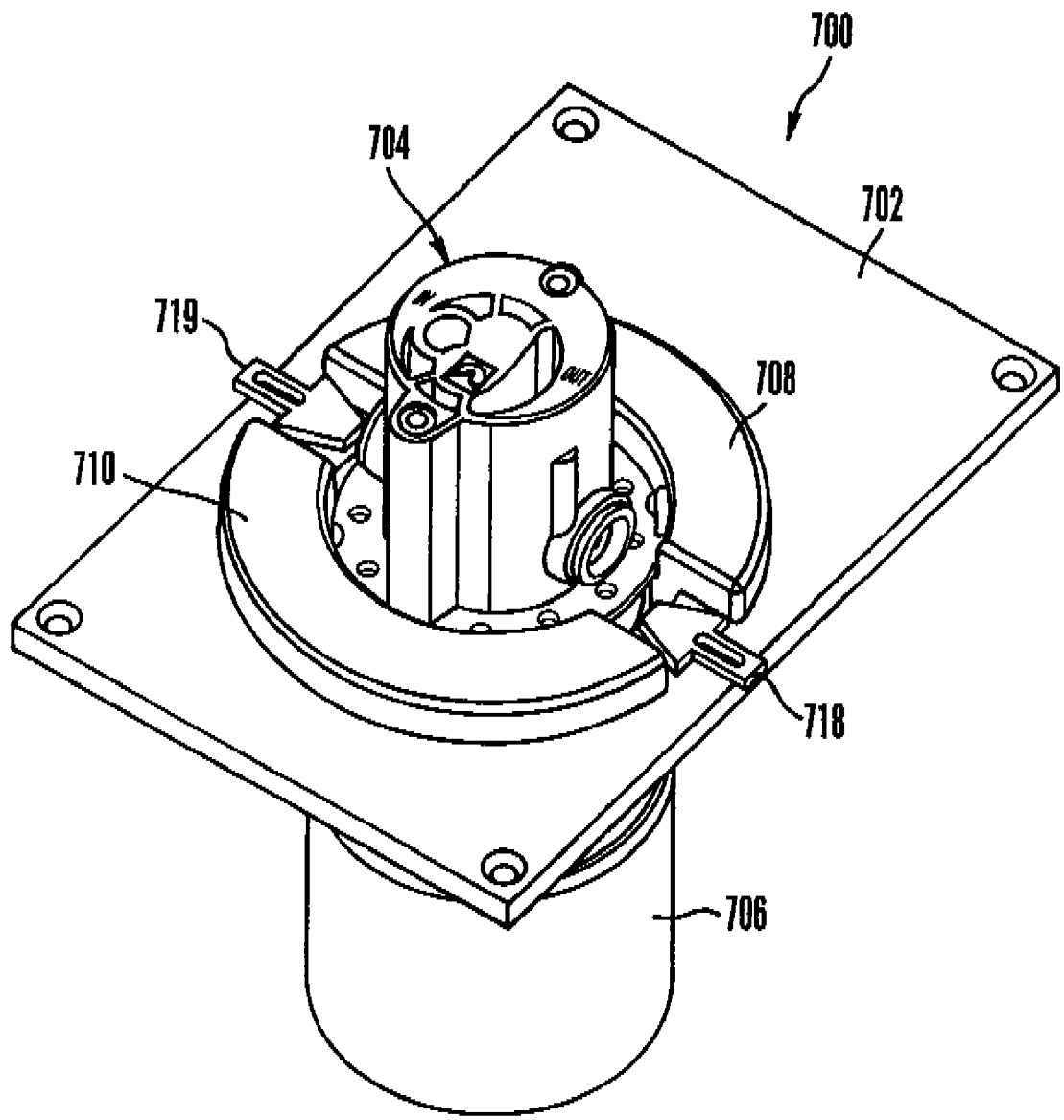
FIG. 17 is a perspective view of an alternative saline pump assembly.
Figure 18:
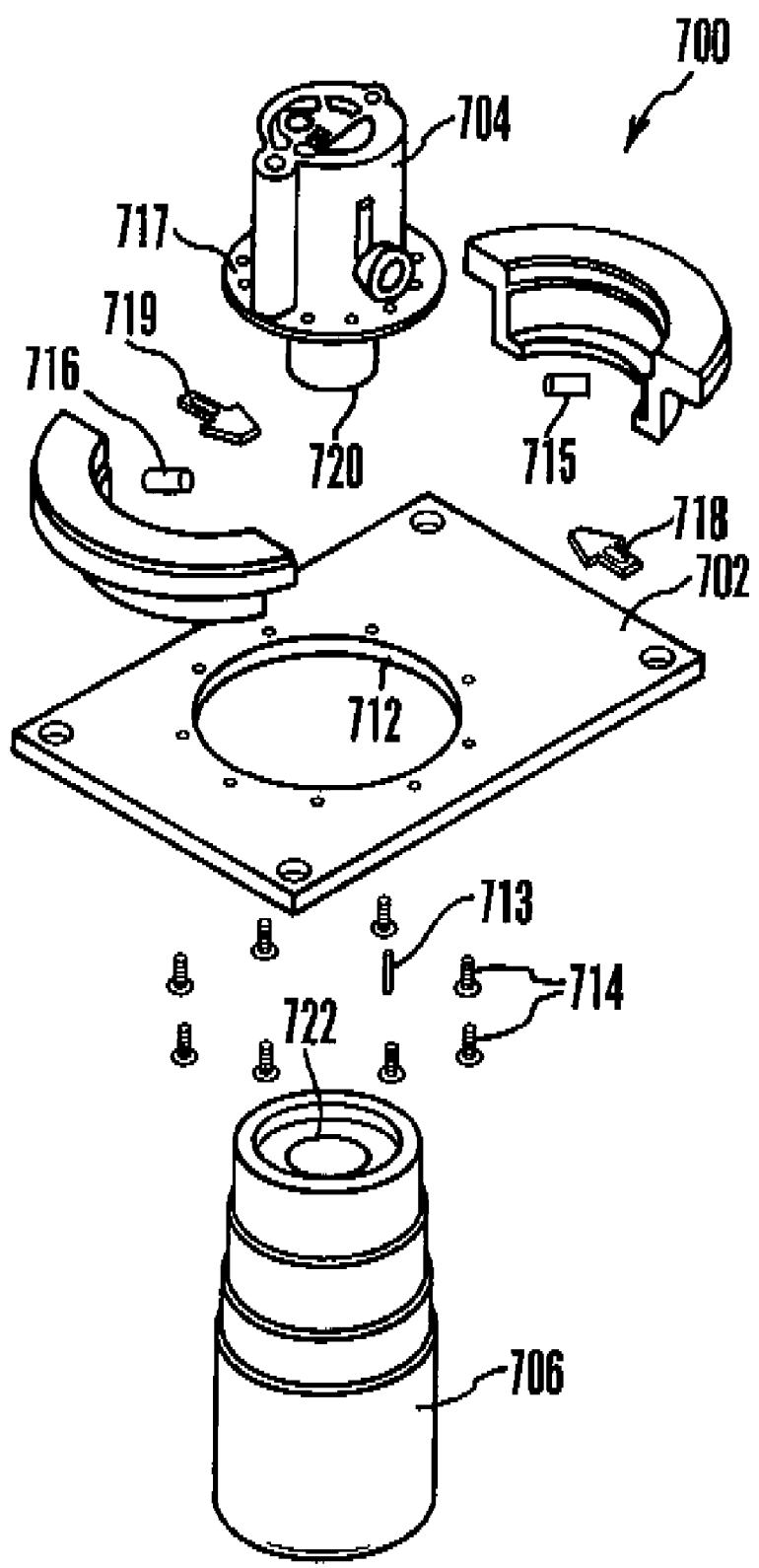
FIG. 18 is an exploded view of the alternative saline pump assembly.

In an alternative embodiment, as shown in FIGS. 17 and 18, a saline pump assembly 700 includes a pump support platform 702 and a positive displacement gear pump 704. In non-limiting embodiments, the gear pump 704 can incorporate some or all of the features set forth in U.S. Pat. Nos. 6,270,324; 6,210,138; 6,158,994; 5,494,416; 5,219,274; 5,165,868; and 4,065,235, all of which are incorporated herein by reference. As shown in FIGS. 17 and 18, the pump support platform 702 includes a pump drive motor 706 that is preferably a brushless, direct current motor.

FIGS. 17 and 18 show that the pump support platform 702 includes a first support collar 708 and a second support collar 710 that fit into a generally cylindrical pump locking bore 712 formed in the support platform 702. Plural fasteners 714 can be used to affix the support collars 708, 710 to the support platform 702. It is to be understood that the gear pump 704 fits into the support collars after they are inserted in the bore 712. As shown in FIG. 18, a first spring loaded ball plunger 715 and a second spring loaded ball plunger 716 are provided and can be used to removably engage the gear pump 704 with the support platform 702. One or more alignment pins 713 can be used to properly align the gear pump 704 when it is engaged with the support platform 702. When the gear pump 704 is installed in the support platform 702, the ball plungers 715, 716 engage a metal flange 717 around the gear pump 704 and provide a downward force on the metal flange 717 in order to keep the gear pump 704 installed in the support platform 702.

As shown in FIGS. 17 and 18, a first optical sensor 718 and a second optical sensor 719 are installed on the upper surface of the support platform 702 and can be used to detect the presence of the gear pump 704 on the support platform 702. It is to be understood that each optical sensor 718, 719 includes an emitter (not shown) and a detector (not shown) that are configured to transmit an optical signal toward the space in which the gear pump 704 occupies when it is properly installed and detect reflection from the gear pump 704 when it is, indeed, properly installed.

FIG. 18 further shows that the gear pump 704 includes a cylindrical magnet 720 that extends from the gear pump 704. It is to be understood that the cylindrical magnet 720 is attached to a drive shaft (not shown) within the gear pump 704 and as the cylindrical magnet 720 rotates it rotates the drive shaft. Further, the motor 706 includes a cup-shaped magnet 722 that is sized and shaped to receive the cylindrical magnet 720 and magnetically engage the cylindrical magnet 720. The cup-shaped magnet 722 is coupled to a drive shaft (not shown) within the motor 706 and the motor 706 can be energized to rotate the cup-shaped magnet 722.

With this structure, the gear pump 704 can be removably engaged with the support platform 702. When the gear pump 704 is engaged with the support platform 702, the cylindrical magnet 720 is magnetically coupled to the cup-shaped magnet 722. Accordingly, as the cup-shaped magnet 722 is rotated by the motor 706 it causes the cylindrical magnet 720 to rotate and which, in turn, causes the gear pump 704 to pump fluid therethrough.

It is to be understood that for overpressure protection, the gear pump 704 includes a bypass relief valve (not shown) that opens on high pressure. In lieu of a bypass relief valve, the magnets 720, 722 can be magnetized such that the magnetic coupling established therebetween can be broken under conditions of overpressure. Moreover, the speed of the pump 704 can be established for the desired heat exchange rate.

Description of a Preferred Saline Flow Detector

Figure 19:
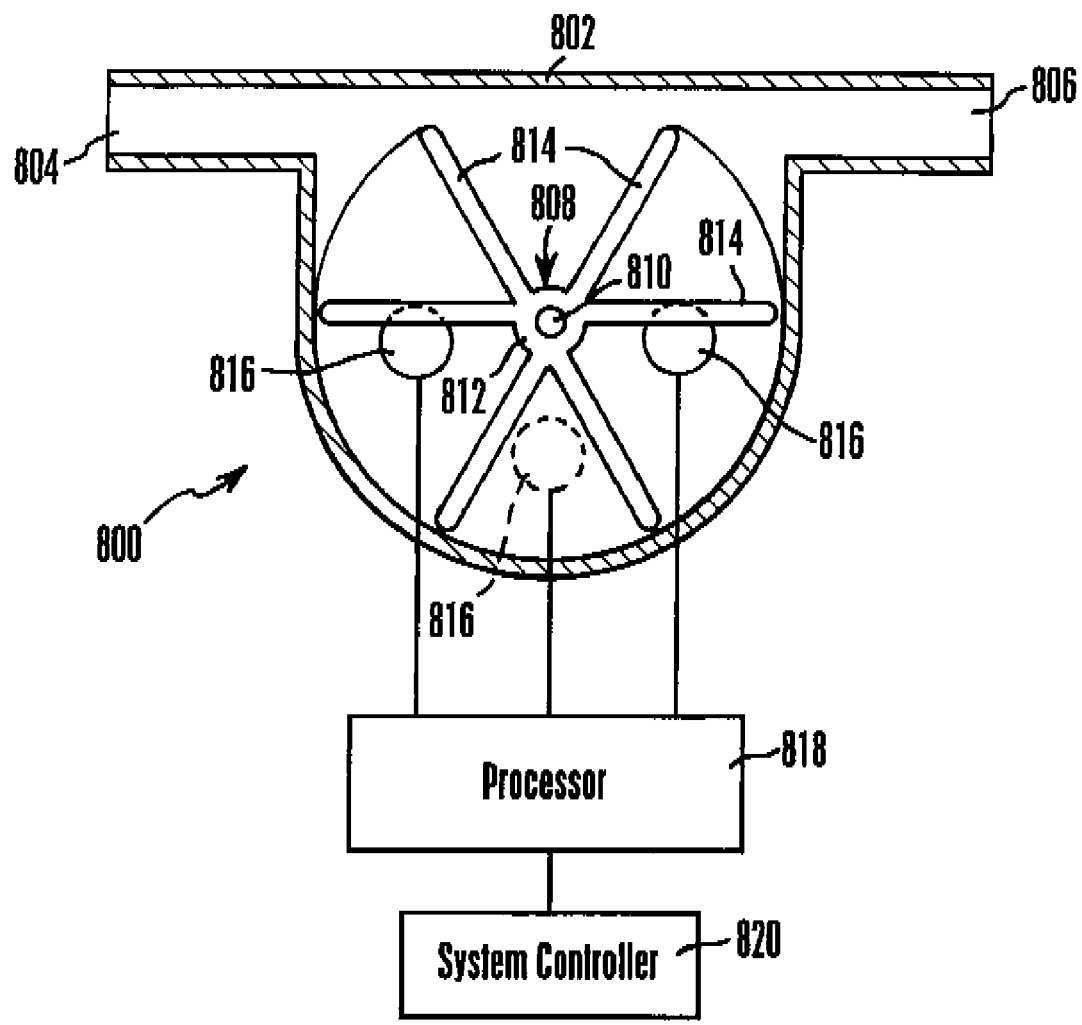
FIG. 19 is a side plan view of a preferred flow detector.

Referring now to FIG. 19, a preferred, non-limiting embodiment of a saline flow detector is shown and generally designated 800. As shown in FIG. 19, the flow detector 800 includes a preferably clear, plastic housing 802 having an inlet 804 and an outlet 806. A lightweight, preferably plastic paddle wheel 808 is installed within the housing 802 on an axle 810. FIG. 19 shows that the paddle wheel 808 includes a central hub 812 from which preferably three opaque, plastic paddles 814 extend radially (it is to be understood that each paddle 814 includes a pair of opposing paddle blades). As shown, the paddles 814 are positioned around the hub 812 approximately one-hundred and twenty degrees (120°) from each other. It can be appreciated that fluid flowing from the inlet 804 to the outlet 806 flows tangential to the paddle wheel 808 and causes it to spin. Moreover, three opaque walls 815 are formed around the paddle wheel 808 between alternating pairs of adjacent paddle blades.

As shown in FIG. 19, preferably three infrared transmitter/receiver light emitting diode (IR T/R LED) pairs 816 can be placed such that the housing 802 is between each IR T/R LED pair 816 and each JR T/R LED pair 816 can send and receive a signal through the housing 802 across the paddle wheel 808 to detect rotation of the paddle wheel 808 when fluid flows through the housing 802. In a preferred embodiment, the IR T/R LED pairs 816 are positioned on an imaginary circle concentric with the axle 810. Moreover, the IR T/R LED pairs are arranged so that a center pair 816 is aligned with the axle 810 and two side pairs 816 flank the center pair 816. Each side pair is approximately plus-or-minus sixty-four degrees (±64°) from the center pair 816 on the imaginary circle. This arrangement insures that that regardless of the position of the pin wheel 808, one of the three signal paths established by the IR T/R LED pairs 816 through the housing 802 is always unblocked by the paddle wheel 808.

FIG. 19 further shows that each IR T/R LED pair 816 is connected to a processor 818 that, in turn, is connected to a system controller 820. The processor 818 includes a program that, based on the signals received from the IR T/R LED pairs 816, allows the processor 818 to determine if the paddle wheel 808 is rotating and fluid is flowing through the housing and accordingly, the working fluid circuit. If not, an alarm can be activated.

Description of the Saline Flow Detection Logic

Figure 20:
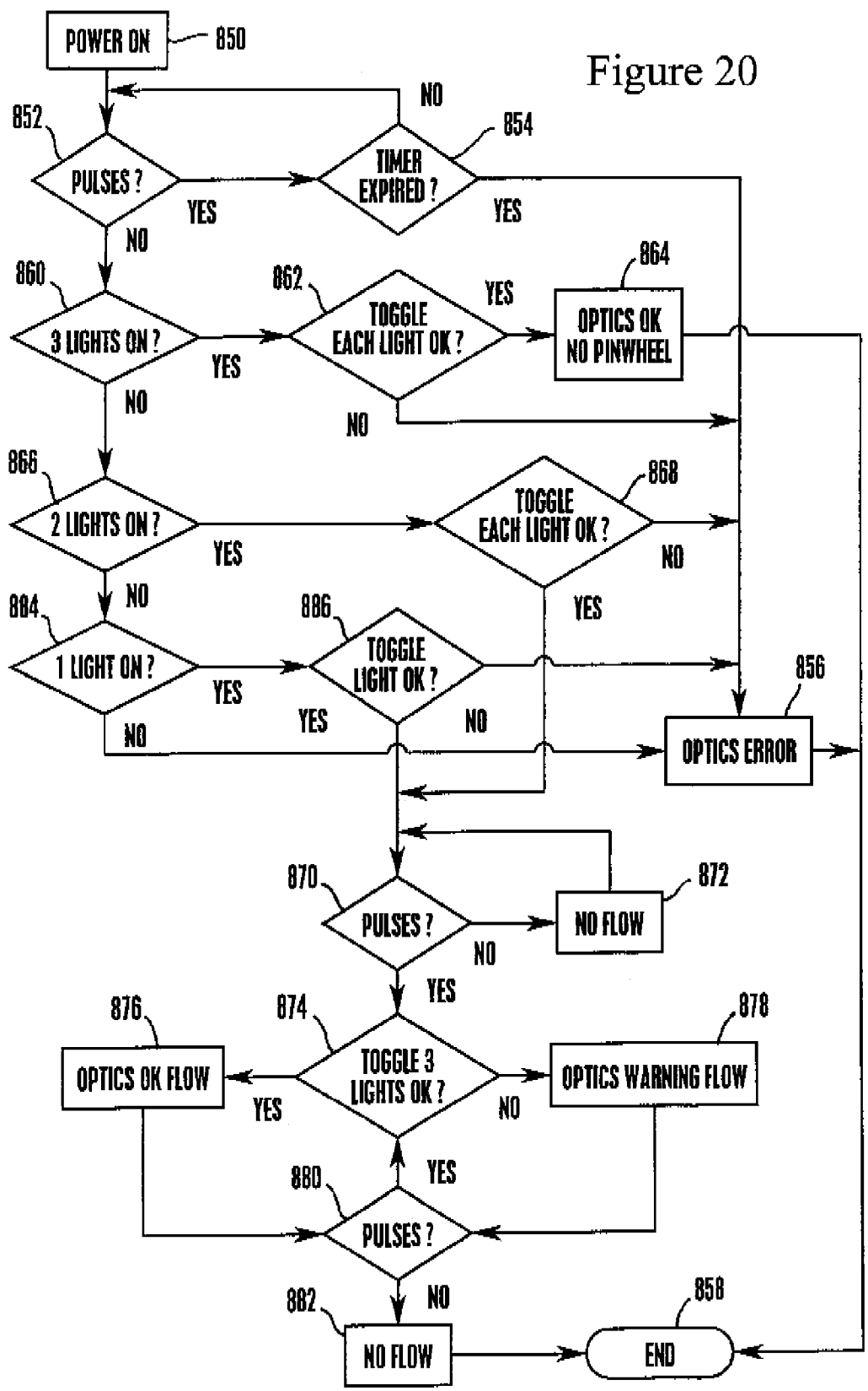
FIG. 20 is flow chart of the saline flow detection logic.

FIG. 20 shows the saline flow detection logic that commences at block 850 wherein the flow detector 800 is energized, i.e., its power is turned on. Moving to decision diamond 852, it is determined whether pulses are being received at the processor 818. The pulses represent motion of the paddle wheel 808, i.e., the motion of the paddles through the light beams established by the IR T/R LED pairs 816. If there are indeed pulses, the logic moves to decision diamond 854 where it is determined whether a timer has expired. If the timer has not expired, the logic loops back to decision diamond 852 and continues as described above. If so, the logic moves to block 856 and an "optics error" message is presented to the user. The logic then ends at state 858.

Returning to decision diamond 852, if pulses are not present, the logic moves to decision diamond 860 where it is determined whether all three IR T/R LED pairs 816 are on. If so, the logic moves to decision diamond 862 where it is determined if all three IR T/R LED pairs 816 are operating properly. This can be determined, e.g., by sequentially toggling the IR T/R LED pairs 816 on and off. If it is determined that the IR T/R LED pairs 816 are not operating property, the logic moves to block 856 where an "optics error" message is presented to the user. The logic then ends at state 858. Otherwise, an "optics ok, no pinwheel" message is presented to the user. The logic then ends at state 858.

At decision diamond 860, if all three IR T/R LED pairs 816 are not on, the logic moves to decision diamond 866 where it is determined if two out of three of the IR T/R LED pairs 816 are on. If so, the logic moves to decision diamond 868 where it is determined whether the two IR T/R LED pairs 816 are operating properly, e.g., by toggling the two IR T/R LED pairs 816 on and off. If the two IR T/R LED pairs 816 are not operating properly, the logic moves to block 856 where an "optics error" message is presented to the user. The logic then ends at state 858. Otherwise, if the two IR T/R LED pairs 816 are operating properly, the logic moves to decision diamond 870 where it is determined if signal pulses are present. If not, the logic moves to block 872 where a "no flow" message is presented to the user. The logic then loops back to decision diamond 870.

At decision diamond 870, if pulses are present, the logic moves to decision diamond 874 where it is determined if all three IR T/R LED pairs 816 are operating properly. If so, an "optics ok, flow" message is indicated to the user at block 876. Otherwise, an "optics warning, flow" message is indicated to the user at block 878. From block 876 or block 878, the logic moves to block 880 where it is determined if pulses are present. If pulses are indeed present, the logic returns to decision diamond 874 and continues as described above. Conversely, if pulses are not present, the logic proceeds to block 882 where a "no flow" message is presented to the user. The logic then ends at state 858.

Returning to decision diamond 866, if it is determined that two IR T/R LED pairs 816 are not on, the logic continues to decision diamond 884 where it is determined if one IR T/R LED pair 816 is on. If not, the logic proceeds to block 856 where an "optics error" is presented to the user. The logic then ends at state 858. If the IR T/R LED pair 816 is on, the logic moves to decision diamond 886 where it is determined whether the IR T/R LED pair 816 is operational. If the IR T/R LED pair 816 is not operational, the logic continues to block 856 where an "optics error" is presented to the user. The logic then ends at state 858. If the IR T/R LED pair 816 is operating properly, the logic moves to decision diamond 870 and continues as described above.

With the above logic, the flow detector 800 can indicate flow through the working fluid circuit only if signal pulses are output by the flow detector 800. Moreover, while the paddle wheel 808 is rotating, the processor 818 is constantly testing each of the IR T/R LED pairs 816 by sequentially toggling each of the IR T/R LED pairs 816 on and off and reading the signals output thereby.

Description of the Glycol Flow Detection Logic

Figure 21:
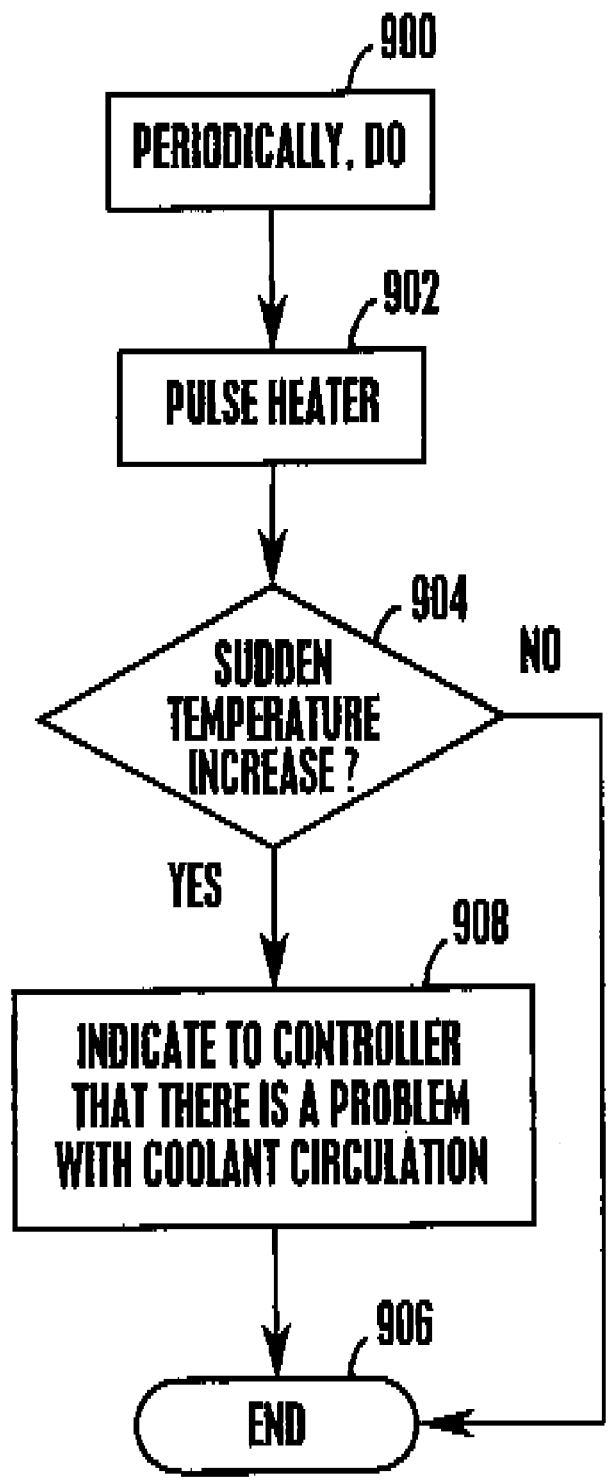
FIG. 21 is flow chart of the glycol flow detection logic.

Referring now to FIG. 21, the glycol flow detection logic is shown and commences at block 900 with a do loop wherein periodically, the following steps are performed. At block 902, the heater 166 (FIG. 4) is periodically pulsed. Moving to decision diamond 904, it is determined if there is a sudden increase in temperature (e.g., above a predetermined quantity), as indicated by the thermocouple temperature sensor 170 (FIG. 4). If not, the logic ends at state 906. Otherwise, the logic proceeds to block 908 where it is indicated to a controller that there is a problem with the glycol circulation. It can be appreciated that in response to the indication of a problem, the controller can shut off power to the heater at block 910.

Relevant Equations

As described above, the power required to cool the patient can be viewed at the display device 98. It is to be understood that the power equation described below is most accurate for a patient having a weight of approximately seventy-five kilograms (75 kg). Accordingly, the power used to cool a patient can be determined using the following equation:

$$\left(\frac{dT_{pt}/dt \text{ ° C./min} \times 60 \text{ min/}hr}{1.4 \text{ ° C./}hr}\right) \times 100w \times (-1)$$

where:

$dT_{pt}/dt$ is determined by the equation disclosed above.

While the particular HEATING/COOLING SYSTEM FOR INDWELLING HEAT EXCHANGE CATHETER as herein shown and described in detail is fully capable of attaining the above-described aspects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. A fluid pump assembly, comprising: a pump support platform supporting a motor; and a pump removably engaged with the pump support platform, the pump pumping working fluid to and from an intravascular catheter, the motor being removably coupled to the pump to provide power to the pump when the pump is engaged with the pump support platform, wherein the pump support platform includes a quick-release locking arm that prevents the pump from being disengaged with the pump support platform unless the locking arm is rotated to release the pump, wherein the pump support platform is formed with a generally cylindrical pump locking bore formed with a first slot, a second slot, and a third slot, each slot terminating in a respective bay, the pump including a housing supporting first, second, and third legs alignable with the respective bays such that the pump can be moved toward the pump support platform until the legs are within their respective bays, the pump being then rotatable by hand until each leg of the pump reaches a respective end of each slot, wherein during installation of the pump on the pump support platform, at least one leg of the pump rides against and then past the quick-release locking arm until the quick-release locking arm clears the leg and snaps under spring bias to a position to prevent the pump from being removed from the pump support platform.

2. The pump assembly of claim 1, wherein the pump locking bore removably engages the pump.

3. The system of claim 1, wherein the pump is a diaphragm pump.

4. The system of claim 1, wherein the pump support platform includes an overflow bore through which any saline that may leak from the pump can flow.

* * * * *